United States Patent
Wang et al.

(10) Patent No.: US 10,928,401 B2
(45) Date of Patent: Feb. 23, 2021

(54) METHODS AND SYSTEMS FOR DIAGNOSING DISEASES

(71) Applicant: Newomics Inc., Berkeley, CA (US)

(72) Inventors: Daojing Wang, Moraga, CA (US); Pan Mao, Milpitas, CA (US)

(73) Assignee: NEWOMICS INC., Berkeley, CA (US)

(*) Notice: Subject to any disclaimer, the term of this patent is extended or adjusted under 35 U.S.C. 154(b) by 0 days.

(21) Appl. No.: 16/412,039

(22) Filed: May 14, 2019

(65) Prior Publication Data
US 2020/0081014 A1    Mar. 12, 2020

Related U.S. Application Data

(63) Continuation of application No. 15/203,666, filed on Jul. 6, 2016, now Pat. No. 10,338,079, which is a (Continued)

(51) Int. Cl.
*G01N 33/68* (2006.01)
*G01N 33/72* (2006.01)
(Continued)

(52) U.S. Cl.
CPC .... *G01N 33/6848* (2013.01); *B01L 3/502707* (2013.01); *B01L 3/502715* (2013.01);
(Continued)

(58) Field of Classification Search
CPC .............. B01L 2200/10; B01L 2200/12; B01L 2300/0627; B01L 2300/0681; B01L 2300/0816; B01L 2300/0867; B01L 2300/0874; B01L 2300/0887; B01L 3/0268; B01L 3/502707; B01L 3/502715; B01L 3/502761; G01N 1/28; G01N 2570/00; G01N 2800/042; G01N 2800/56; G01N 30/6095; G01N 30/72; G01N 30/7266; G01N 33/6848; G01N 33/6893; G01N 33/721; G01N 33/723; G01N 33/726;
(Continued)

(56) References Cited

U.S. PATENT DOCUMENTS 7,906,758 B2    3/2011 Stults et al.
8,022,361 B2    9/2011 Wang et al.
(Continued)

FOREIGN PATENT DOCUMENTS

WO  WO-2014093080 A1   6/2014
WO  WO-2015112429 A1   7/2015
WO  WO-2016183521 A1   11/2016

OTHER PUBLICATIONS

Chen, et al. Qualitative and quantitative analysis of tumor cell metabolism via stable isotope labeling assisted microfluidic chip electrospray ionization mass spectrometry. Anal Chem. Feb. 7, 2012;84(3):1695-701. doi: 10.1021/ac300003k. Epub Jan. 24, 2012.
(Continued)

*Primary Examiner* — Maureen Wallenhorst
(74) *Attorney, Agent, or Firm* — Wilson Sonsini Goodrich & Rosati

(57) ABSTRACT

The present disclosure provided methods and systems for diagnosing diseases and monitoring their progression and therapeutic responses by detecting a presence or absence, or an increase or decrease, of one or more substances in a sample.

21 Claims, 13 Drawing Sheets

Related U.S. Application Data continuation of application No. PCT/US2015/011643, filed on Jan. 15, 2015.

(60) Provisional application No. 61/930,595, filed on Jan. 23, 2014.

(51) Int. Cl.
| | |
|---|---|
| *G01N 33/92* | (2006.01) |
| *B01L 3/00* | (2006.01) |
| *G01N 30/60* | (2006.01) |
| *G01N 30/72* | (2006.01) |
| *G01N 33/66* | (2006.01) |
| *G01N 1/28* | (2006.01) |
| *B01L 3/02* | (2006.01) |

(52) U.S. Cl.
CPC .... *B01L 3/502761* (2013.01); *G01N 30/6095* (2013.01); *G01N 30/72* (2013.01); *G01N 30/7266* (2013.01); *G01N 33/6893* (2013.01); *G01N 33/723* (2013.01); *G01N 33/726* (2013.01); *G01N 33/92* (2013.01); *B01L 3/0268* (2013.01); *B01L 2200/10* (2013.01); *B01L 2200/12* (2013.01); *B01L 2300/0627* (2013.01); *B01L 2300/0681* (2013.01); *B01L 2300/0816* (2013.01); *B01L 2300/0867* (2013.01); *B01L 2300/0874* (2013.01); *B01L 2300/0887* (2013.01); *G01N 1/28* (2013.01); *G01N 33/66* (2013.01); *G01N 33/68* (2013.01); *G01N 2570/00* (2013.01); *G01N 2800/042* (2013.01); *G01N 2800/56* (2013.01)

(58) Field of Classification Search
CPC ........ G01N 33/92; G01N 33/48; G01N 33/49; G01N 33/66; Y10T 436/24; Y10T 436/25; Y10T 436/25375; Y10T 436/255; Y10T 436/2575
USPC ...... 436/63, 66, 67, 86, 87, 88, 94, 95, 173, 436/174, 177, 178, 180, 161; 422/70, 422/502, 503, 508, 527
See application file for complete search history.

(56) References Cited

U.S. PATENT DOCUMENTS

| | | |
|---|---|---|
| 9,518,963 B2 | 12/2016 | Prentice et al. |
| 9,793,477 B2 | 10/2017 | Wang et al. |
| 10,338,079 B2 | 7/2019 | Wang et al. |
| 10,627,395 B2 | 4/2020 | Wang et al. |
| 2003/0027347 A1 | 2/2003 | Shapiro |
| 2004/0113068 A1 | 6/2004 | Bousse et al. |
| 2011/0250618 A1 | 10/2011 | Nelson et al. |
| 2011/0256580 A1 | 10/2011 | Kim et al. |
| 2014/0110661 A1 | 4/2014 | Wang et al. |
| 2014/0322723 A1 | 10/2014 | Halperin et al. |
| 2015/0293063 A1 | 10/2015 | Wang et al. |
| 2018/0038850 A1 | 2/2018 | Wang et al. |

OTHER PUBLICATIONS

Chen, et al. Quantitation of Intact Proteins in Human Plasma Using Top-Down Parallel Reaction Monitoring—MS. Anal Chem. Sep. 18, 2018;90(18):10650-10653. doi: 10.1021/acs.analchem.8b02699. Epub Sep. 7, 2018.
Fortier, et al. Integrated microfluidic device for mass spectrometry-based proteomics and its application to biomarker discovery programs. Send toAnal Chem. Mar. 15, 2005;77(6):1631-40.
Gao, et al. Characterization of drug permeability in Caco-2 monolayers by mass spectrometry on a membrane-based microfluidic device. Lab Chip. Mar. 7, 2013;13(5):978-85. doi: 10.1039/c2lc41215b. Epub Jan. 23, 2013.
Gasilova, et al.Microchip emitter for solid-phase extraction-gradient elution-mass spectrometry. Anal Chem. Jul. 2, 2013;85(13):6254-63. doi: 10.1021/ac400171e. Epub Jun. 18, 2013.
Han, et al. Binding of perfluorooctanoic acid to rat and human plasma proteins. Chem Res Toxicol. Jun. 2003;16(6):775-81.
International search report and written opinion dated Apr. 24, 2015 for PCT/US2015/011643.
International Search Report dated Aug. 19, 2016 for International Application No. PCT/US2016/032544.
Jung, et al. Microchip electrospray: improvements in spray and signal stability during gradient elution by an inverted postcolumn makeup flow. Anal Chem. Dec. 1, 2011;83(23):9167-73. doi: 10.1021/ac202413z. Epub Nov. 9, 2011.
Kim, et al. Microfabricated monolithic multinozzle emitters for nanoelectrospray mass spectrometry. Anal Chem. May 15, 2007;79(10):3703-7. Epub Apr. 20, 2007.
Kuklenyik, et al. Automated solid-phase extraction and measurement of perfluorinated organic acids and amides in human serum and milk. Environ Sci Technol. Jul. 1, 2004;38(13):3698-704.
Kuklenyik, et al. Measurement of 18 perfluorinated organic acids and amides in human serum using on-line solid-phase extraction. Anal Chem. Sep. 15, 2005;77(18):6085-91.
Lau, et al. Perfluoroalkyl acids: a review of monitoring and toxicological findings. Toxicol Sci. Oct. 2007;99(2):366-94. Epub May 22, 2007.
Lee, et al. Microfluidic mixing: a review. Int J Mol Sci. 2011;12(5):3263-87. doi: 10.3390/ijms12053263. Epub May 18, 2011.
Li, et al. Profiling Cys34 adducts of human serum albumin by fixed-step selected reaction monitoring. Mol Cell Proteomics. Mar. 2011;10(3):M110.004606. doi: 10.1074/mcp.M110.004606. Epub Dec. 30, 2010.
Malinsky, et al. Determination of perfluorinated compounds in fish fillet homogenates: method validation and application to fillet homogenates from the Mississippi River. Anal Chim Acta. Jan. 10, 2011;683(2):248-57. doi: 10.1016/j.aca.2010.10.028. Epub Nov. 3, 2010.
Mao, et al., Biomonitoring of Perfluorinated Compounds in a Drop of Blood. Environ. Sci. Technol., 2015, 49 (11), pp. 6808-6814.
Mao, et al. Multinozzle emitter array chips for small-volume proteomics. Anal Chem. Jan. 15, 2013;85(2):816-9. doi: 10.1021/ac3032965. Epub Dec. 21, 2012.
Mao, et al. Multinozzle emitter arrays for nanoelectrospray mass spectrometry. Anal Chem. Aug. 1, 2011;83(15):6082-9. doi: 10.1021/ac2011813. Epub Jul. 5, 2011.
Mao, et al. Strategy for signaling molecule detection by using an integrated microfluidic device coupled with mass spectrometry to study cell-to-cell communication. Anal Chem. Jan. 15, 2013;85(2):868-76. doi: 10.1021/ac303164b. Epub Dec. 31, 2012.
Mao, et al. Top-down proteomics of a drop of blood for diabetes monitoring. J Proteome Res. Mar. 7, 2014;13(3):1560-9. doi: 10.1021/pr401074t. Epub Feb. 17, 2014.
Nakamura, et al. The endogenous exposome. DNA Repair (Amst). Jul. 2014;19:3-13. doi: 10.1016/j.dnarep.2014.03.031. Epub Apr. 24, 2014.
Ouyang, et al. Nondestructive sampling of living systems using in vivo solid-phase microextraction. Chem Rev. Apr. 13, 2011;111(4):2784-814. doi: 10.1021/cr100203t. Epub Jan. 27, 2011.
Phinney, et al. An, et al. Development of a Standard Reference Material for metabolomics research. Anal Chem. Dec. 17, 2013;85(24):11732-8. doi: 10.1021/ac402689t. Epub Dec. 3, 2013.
Rappaport, et al. Adductomics: characterizing exposures to reactive electrophiles. Toxicol Lett. Aug. 13, 2012;213(1):83-90. doi: 10.1016/j.toxlet.2011.04.002. Epub Apr. 8, 2011.
Rappaport, et al. The blood exposome and its role in discovering causes of disease. Environ Health Perspect. Aug. 2014;122(8):769-74. doi: 10.1289/ehp.1308015. Epub Mar. 21, 2014.
Reiner, et al. Determination of perfluorinated compounds in human plasma and serum Standard Reference Materials using independent analytical methods. Anal Bioanal Chem. Nov. 2011;401(9):2899-907. doi: 10.1007/s00216-011-5380-x. Epub Sep. 9, 2011.

(56) References Cited

OTHER PUBLICATIONS

Renner. Growing concern over perfluorinated chemicals. Environ Sci Technol. Apr. 1, 2001;35(7):154A-160A.
U.S. Appl. No. 15/203,666 Office Action dated Feb. 8, 2019.
U.S. Appl. No. 15/203,666 Notice of Allowance dated Apr. 19, 2019.
U.S. Appl. No. 15/203,666 Office Action dated Sep. 18, 2018.
U.S. Appl. No. 15/786,949 Office Action dated Oct. 8, 2019.
Vuckovic, et al. Solid-phase microextraction in bioanalysis: New devices and directions. J Chromatogr A. Jun. 18, 2010;1217(25):4041-60. doi: 10.1016/j.chroma.2009.11.061. Epub Dec. 4, 2009.
Wang, et al. Single cell analysis: the new frontier in 'omics'. Trends Biotechnol. Jun. 2010;28(6):281-90. doi: 10.1016/j.tibtech.2010.03.002. Epub Apr. 29, 2010.
Yang, et al. Coupling on-chip solid-phase extraction to electrospray mass spectrometry through an integrated electrospray tip. Electrophoresis. Oct. 2005;26(19):3622-30.
Ying, et al. Microfluidic chip-based technologies: emerging platforms for cancer diagnosis. BMC Biotechnol. Sep. 27, 2013;13:76. doi: 10.1186/1472-6750-13-76.
Yu, et al. Monolithic porous polymer for on-chip solid-phase extraction and preconcentration prepared by photoinitiated in situ polymerization within a microfluidic device. Anal Chem. Nov. 1, 2001;73(21):5088-96.
U.S. Appl. No. 15/786,949 Notice of Allowance dated Feb. 20, 2020.

FIG. 1a
(i) Top view
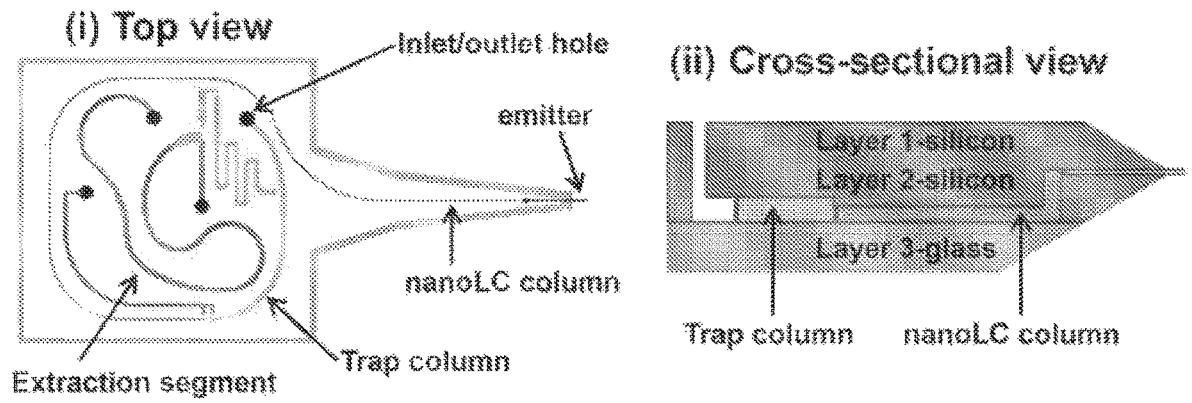
(ii) Cross-sectional view
(i) Chip assembly
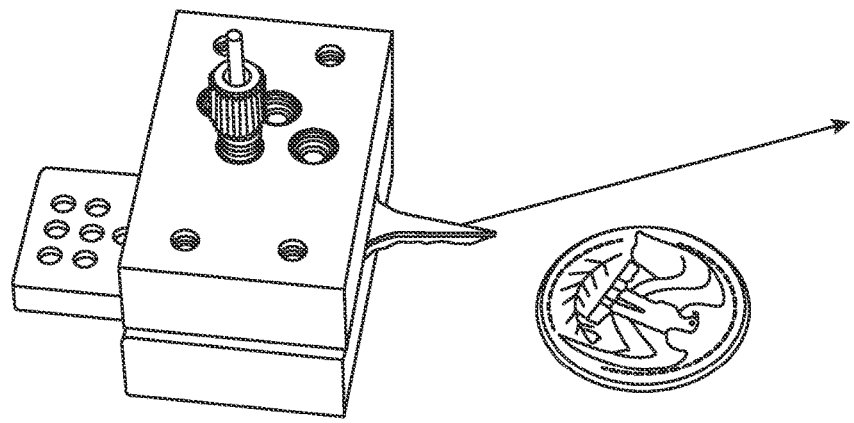
(ii)
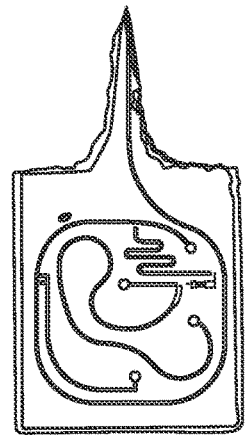
FIG. 1b

METHODS AND SYSTEMS FOR DIAGNOSING DISEASES

CROSS-REFERENCE

This application is a Continuation of U.S. patent application Ser. No. 15/203,666, filed Jul. 6, 2016, now U.S. Pat. No. 10,338,079, which is a Continuation of International Patent Application No. PCT/US2015/011643, filed Jan. 15, 2015, which claims the benefit of U.S. Provisional Patent Application No. 61/930,595, filed Jan. 23, 2014, each of which is incorporated herein by reference in its entirety.

STATEMENT OF GOVERNMENT SUPPORT

This invention was made with government support under grant numbers ES022360, ES023529, GM109682, AT008297, AG046025, and AI106100, and contract number HHSN261201300033C awarded by the National Institutes of Health. The government has certain rights in the invention.

BACKGROUND

The proteome may be reflective of the physiological and pathological states of a subject. Proteomics is a powerful tool for diagnostics of diseases and monitoring of therapeutic responses. The majority of current protein assays in clinical settings are based on enzyme-linked immunosorbent assay (ELISA) immunoassays, which may require high-quality antibodies and may be hard to achieve with high multiplexing (e.g., greater than 10) due to the cross-reactivity of antibodies. Mass spectrometry (MS) measures the mass-to-charge ratio of charged species and may be an enabling technology for proteomics. Aside from de novo identification of target proteins, MS has advantages over ELISA for detecting protein mutations, modification, truncations, and adductations, for example, once combined with the liquid chromatography (LC), liquid chromatography mass spectrometry (LC-MS) may enable separation, identification, characterization, and quantitation of complex mixtures of proteins and peptides and their isoforms.

SUMMARY

Recognized herein are various issues with systems currently available for disease detection, diagnosis and/or monitoring. For instance, current mass spectrometry systems may require substantially large sample sizes, which make such systems impractical for use in various diagnostics applications, including point of care applications. Accordingly, recognized herein is a need for a platform that can achieve robustness, sensitivity, and throughput for analysis of small-volume samples (or biospecimens).

The present disclosure provides systems and methods for biological sample analysis and disease detection and/or monitoring. Systems provided herein can enable the detection and/or monitoring of a disease in a relatively short timeframe using biological samples of substantially small volume.

An aspect of the present disclosure provides a method for detecting a presence of a plurality of biomarkers in a biological sample of a subject, comprising: (a) providing a microfluidic device including a fluid channel in fluid communication with at least one emitter having a plurality of nozzles that are operatively coupled to a detector, wherein the fluid channel includes a separation medium that is adapted to separate the plurality of biomarkers into subsets of biomarkers along the fluid channel, and wherein the detector is adapted to generate signals that are indicative of each of the subsets of biomarkers; (b) directing the biological sample having a volume less than or equal to about 50 microliters through the fluid channel to the at least one emitter under conditions that permit the plurality of biomarkers to be separated into the subsets of biomarkers along the fluid channel; (c) directing at least a portion of the biological sample from the plurality of nozzles to the detector, wherein the detector generates signals upon exposure to the at least the portion of the biological sample; and (d) detecting a presence of the subsets of biomarkers based on the signals generated in (c) to detect the presence of the plurality of biomarkers in the biological sample.

In some embodiments of aspects provided herein, the microfluidic device is part of a disposable chip. In some embodiments of aspects provided herein, the microfluidic device is separate from the detector. In some embodiments of aspects provided herein, the nozzles extend from a base tube having a larger cross-sectional dimension than the nozzles, and the base tube is in fluid communication with the fluid channel. In some embodiments of aspects provided herein, the nozzles are nanotubes or microtubes. In some embodiments of aspects provided herein, the nozzles and the base tube are monolithic. In some embodiments of aspects provided herein, the nozzles have a cross-sectional dimension that is less than or equal to about 50 micrometers. In some embodiments of aspects provided herein, the cross-sectional dimension is less than or equal to about 25 micrometers. In some embodiments of aspects provided herein, the cross-sectional dimension is less than or equal to about 10 micrometers. In some embodiments of aspects provided herein, the microfluidic device comprises a first substrate adjacent to a second substrate, and the emitter is disposed between the first substrate and the second substrate. In some embodiments of aspects provided herein, the first substrate is formed of silicon. In some embodiments of aspects provided herein, the second substrate is formed of silicon oxide. In some embodiments of aspects provided herein, the separation medium includes beads and/or monolithic porous rod structures. In some embodiments of aspects provided herein, the beads have a cross-sectional dimension from about 1 micrometer to 50 micrometers. In some embodiments of aspects provided herein, the detector is a mass spectrometer. In some embodiments of aspects provided herein, the subsets of biomarkers are detected based on an ionization pattern of the subsets in the mass spectrometer. In some embodiments of aspects provided herein, the mass spectrometer is a quadrupole and/or orthogonal time-of-flight mass spectrometer. In some embodiments of aspects provided herein, the mass spectrometer is an orbitrap.

In some embodiments of aspects provided herein, the method further comprises generating an electronic report that is indicative of the presence of the plurality of biomarkers in the biological sample. In some embodiments of aspects provided herein, the electronic report identifies a presence of a disease in the subject based on the presence of the plurality of biomarkers in the biological sample. In some embodiments of aspects provided herein, the method further comprises providing the electronic report for display on a user interface of an electronic device of a user. In some embodiments of aspects provided herein, the user is the subject. In some embodiments of aspects provided herein, the user is a healthcare provider of the subject. In some embodiments of aspects provided herein, the method further comprises identifying a disease in the subject based on the presence of the plurality of biomarkers in the biological sample. In some embodiments of aspects provided herein, the disease is selected from the group consisting of diabetes, cancer, a degenerative disorder, an autoimmune disorder, and an inflammatory disease. In some embodiments of aspects provided herein, the degenerative disorder is a neurodegenerative disorder. In some embodiments of aspects provided herein, the disease is diabetes. In some embodiments of aspects provided herein, the diabetes is selected from the group consisting of T1D, T2D, and GDM. In some embodiments of aspects provided herein, the plurality of biomarkers includes any two of glycated hemoglobin (HbA1c), glycated albumin (GA) and glucose. In some embodiments of aspects provided herein, the glucose is fasting plasma glucose. In some embodiments of aspects provided herein, the plurality of biomarkers includes all of HbA1c, GA and glucose. In some embodiments of aspects provided herein, the plurality of biomarkers is selected from the group consisting of HSA-Cys, HbA-SNO, GapoA-I and apoA-I MetO. In some embodiments of aspects provided herein, the plurality of biomarkers is indicative of oxidative stress and/or cardiovascular risks of diabetes. In some embodiments of aspects provided herein, the method further comprises detecting the presence of the subsets of biomarkers at multiple time points to monitor a progression of the disease in the subject. In some embodiments of aspects provided herein, the method further comprises providing a therapeutic intervention upon identifying the presence of the plurality of biomarkers in the biological sample. In some embodiments of aspects provided herein, (a)-(d) are performed without obtaining an immediate diagnostic result. In some embodiments of aspects provided herein, detecting the subsets of biomarkers comprises determining a concentration or relative amount of the subsets of biomarkers. In some embodiments of aspects provided herein, the biological sample is a blood sample. In some embodiments of aspects provided herein, the blood sample is a whole blood sample. In some embodiments of aspects provided herein, the blood sample is a plasma sample. In some embodiments of aspects provided herein, the blood sample is a serum sample. In some embodiments of aspects provided herein, the volume is less than or equal to about 40 microliters. In some embodiments of aspects provided herein, the volume is less than or equal to about 30 microliters. In some embodiments of aspects provided herein, the volume is less than or equal to about 20 microliters. In some embodiments of aspects provided herein, the volume is less than or equal to about 10 microliters. In some embodiments of aspects provided herein, the volume is less than or equal to about 5 microliters. In some embodiments of aspects provided herein, the volume is less than or equal to about 1 microliter. In some embodiments of aspects provided herein, each of the subsets of biomarkers includes an individual biomarker among the plurality of biomarkers. In some embodiments of aspects provided herein, the plurality of biomarkers includes one or more proteins. In some embodiments of aspects provided herein, the one or more proteins include one or more glycoproteins. In some embodiments of aspects provided herein, the one or more proteins are selected from the group consisting of glycated hemoglobin (HbA1c), glycated albumin (GA), and glycated apolipoprotein A-1 (GapoA-I). In some embodiments of aspects provided herein, the plurality of biomarkers includes one or more carbohydrates. In some embodiments of aspects provided herein, the one or more carbohydrates include fasting plasma glucose. In some embodiments of aspects provided herein, the plurality of biomarkers includes at least one protein and at least one carbohydrate. In some embodiments of aspects provided herein, (b)-(d) are performed in a time period that is less than or equal to 1 hour. In some embodiments of aspects provided herein, the time period is less than or equal to 30 minutes. In some embodiments of aspects provided herein, the time period is less than or equal to 10 minutes. In some embodiments of aspects provided herein, the time period is less than or equal to 5 minutes. In some embodiments of aspects provided herein, the time period is less than or equal to 1 minute. In some embodiments of aspects provided herein, the plurality of biomarkers includes one or more nucleic acid molecules. In some embodiments of aspects provided herein, the one or more nucleic acid molecules include cell free deoxyribonucleic acid (DNA) and/or cell free ribonucleic acid (RNA). In some embodiments of aspects provided herein, the subsets of biomarkers are detected at a specificity of at least about 80%. In some embodiments of aspects provided herein, the specificity is at least about 90%. In some embodiments of aspects provided herein, the specificity is at least about 95%. In some embodiments of aspects provided herein, the specificity is at least about 99%. In some embodiments of aspects provided herein, the at least one emitter includes a plurality of emitters. In some embodiments of aspects provided herein, the plurality of nozzles includes at least 2 nozzles.

Another aspect of the present disclosure provides a system for detecting a presence of a plurality of biomarkers in a biological sample of a subject, comprising: (a) a detector adapted to generate signals that are indicative of the plurality of biomarkers or subsets thereof; (b) a microfluidic device including at least one fluid channel in fluid communication with at least one emitter having a plurality of nozzles that are operatively coupled to the detector, wherein the fluid channel includes a separation medium that is adapted to separate the plurality of biomarkers into subsets of biomarkers along the fluid channel; and (c) a computer processor coupled to the microfluidic device and programmed to (i) direct the biological sample having a volume less than or equal to about 50 microliters through the fluid channel to the at least one emitter under conditions that permit the plurality of biomarkers to separate into the subsets of biomarkers along the fluid channel, (ii) direct at least a portion of the biological sample from the plurality of nozzles to the detector, wherein the detector generates signals upon contact with the at least the portion of the biological sample, and (iii) detect a presence of the subsets of biomarkers in the biological sample based on the signals generated in (ii) to detect the presence of the plurality of biomarkers in the biological sample.

In some embodiments of aspects provided herein, the microfluidic device is part of a disposable chip. In some embodiments of aspects provided herein, the microfluidic device is a multiplex chip. In some embodiments of aspects provided herein, the multiplex chip is fabricated as a monolithic unit. In some embodiments of aspects provided herein, the multiplex chip is assembled using parallel 1-plex units. In some embodiments of aspects provided herein, the microfluidic device is separate from the detector. In some embodiments of aspects provided herein, the nozzles extend from a base tube having a larger cross-sectional dimension than the nozzles, and the base tube is in fluid communication with the fluid channel. In some embodiments of aspects provided herein, the nozzles are nanotubes or microtubes. In some embodiments of aspects provided herein, the nozzles and the base tube are monolithic. In some embodiments of aspects provided herein, the nozzles have a cross-sectional dimension that is less than or equal to about 50 micrometers. In some embodiments of aspects provided herein, the cross-sectional dimension is less than or equal to about 25 micrometers. In some embodiments of aspects provided herein, the cross-sectional dimension is less than or equal to about 10 micrometers. In some embodiments of aspects provided herein, the microfluidic device comprises a first substrate adjacent to a second substrate, and the emitter is disposed between the first substrate and the second substrate. In some embodiments of aspects provided herein, the fluid channel is between the first substrate and the second substrate. In some embodiments of aspects provided herein, the first substrate includes a plurality of semiconductor layers. In some embodiments of aspects provided herein, the first substrate is formed of silicon. In some embodiments of aspects provided herein, the second substrate is formed of silicon oxide. In some embodiments of aspects provided herein, the separation medium includes beads and/or monolithic porous rod structures. In some embodiments of aspects provided herein, the beads have a cross-sectional dimension from about 1 micrometer to 50 micrometers. In some embodiments of aspects provided herein, the computer processor is programmed to identify a disease in the subject based on the presence of the plurality of biomarkers in the biological sample. In some embodiments of aspects provided herein, the disease is selected from the group consisting of diabetes, cancer, a degenerative disorder, an autoimmune disorder and an inflammatory disease. In some embodiments of aspects provided herein, the degenerative disorder is a neurodegenerative disorder. In some embodiments of aspects provided herein, the disease is diabetes. In some embodiments of aspects provided herein, the diabetes is selected from the group consisting of T1D, T2D and GDM. In some embodiments of aspects provided herein, the plurality of biomarkers includes any two of glycated hemoglobin (HbA1c), glycated albumin (GA) and glucose. In some embodiments of aspects provided herein, the glucose is fasting plasma glucose. In some embodiments of aspects provided herein, the plurality of biomarkers includes all of HbA1c, GA and glucose. In some embodiments of aspects provided herein, the plurality of biomarkers is selected from the group consisting of HSA-Cys, HbA-SNO, GapoA-I and apoA-I MetO. In some embodiments of aspects provided herein, the plurality of biomarkers is indicative of oxidative stress and/or cardiovascular risks of diabetes. In some embodiments of aspects provided herein, the computer processor is programmed to detect the subsets of biomarkers at multiple time points to monitor a progression of the disease in the subject. In some embodiments of aspects provided herein, the detector is a mass spectrometer. In some embodiments of aspects provided herein, the mass spectrometer is a quadrupole and/or orthogonal mass spectrometer. In some embodiments of aspects provided herein, the computer processor is programmed to generate an electronic report that is indicative of the presence of the plurality of biomarkers in the biological sample. In some embodiments of aspects provided herein, the electronic report identifies a presence of a disease in the subject based on the presence of the plurality of biomarkers in the biological sample. In some embodiments of aspects provided herein, the computer processor is programmed to provide the electronic report for display on a user interface of an electronic device of a user. In some embodiments of aspects provided herein, the compute processor is programmed to determine a concentration or relative amount of the subsets of biomarkers. In some embodiments of aspects provided herein, the biological sample is a blood sample. In some embodiments of aspects provided herein, the blood sample is a whole blood sample. In some embodiments of aspects provided herein, the blood sample is a plasma sample. In some embodiments of aspects provided herein, the blood sample is a serum sample. In some embodiments of aspects provided herein, the biological sample has a volume that is less than or equal to about 10 microliters. In some embodiments of aspects provided herein, the volume is less than or equal to about 5 microliters. In some embodiments of aspects provided herein, the volume is less than or equal to about 1 microliter. In some embodiments of aspects provided herein, each of the subsets of biomarkers includes an individual biomarker among the plurality of biomarkers. In some embodiments of aspects provided herein, the plurality of biomarkers includes one or more proteins. In some embodiments of aspects provided herein, the one or more proteins include one or more glycoproteins. In some embodiments of aspects provided herein, the one or more proteins are selected from the group consisting of glycated hemoglobin (HbA1c), glycated albumin (GA) and glycated apolipoprotein A-1 (GapoA-I). In some embodiments of aspects provided herein, the plurality of biomarkers includes one or more carbohydrates. In some embodiments of aspects provided herein, the one or more carbohydrates include fasting plasma glucose. In some embodiments of aspects provided herein, the plurality of biomarkers includes at least one protein and at least one carbohydrate. In some embodiments of aspects provided herein, the computer processor is programed to perform (i)-(iii) in a time period that is less than or equal to 1 hour. In some embodiments of aspects provided herein, the time period is less than or equal to 30 minutes. In some embodiments of aspects provided herein, the time period is less than or equal to 10 minutes. In some embodiments of aspects provided herein, the time period is less than or equal to 5 minutes. In some embodiments of aspects provided herein, the time period is less than or equal to 1 minute. In some embodiments of aspects provided herein, the plurality of biomarkers includes one or more nucleic acid molecules. In some embodiments of aspects provided herein, the one or more nucleic acid molecules include cell free deoxyribonucleic acid (DNA) and/or cell free ribonucleic acid (RNA). In some embodiments of aspects provided herein, the computer processor is programmed to detect the subsets of biomarkers at a specificity of at least about 80%. In some embodiments of aspects provided herein, the specificity is at least about 90%. In some embodiments of aspects provided herein, the specificity is at least about 95%. In some embodiments of aspects provided herein, the specificity is at least about 99%. In some embodiments of aspects provided herein, the at least one emitter includes a plurality of emitters. In some embodiments of aspects provided herein, the plurality of nozzles includes at least 2 nozzles. In some embodiments of aspects provided herein, the microfluidic device includes at least one input in fluid communication with the fluid channel, which input is adapted to receive the biological sample and direct the biological sample to the fluid channel. In some embodiments of aspects provided herein, the microfluidic device includes a plurality of inputs in fluid communication with the fluid channel. In some embodiments of aspects provided herein, the fluid channel includes an enrichment channel and a separation channel downstream of the enrichment channel. In some embodiments of aspects provided herein, the enrichment channel is adapted to fragment and/or concentrate the plurality of biomarkers into the subsets of biomarkers or fragments thereof. In some embodiments of aspects provided herein, the separation channel is adapted to separate the plurality of biomarkers into the subsets of biomarkers.

Another aspect of the present disclosure provides a method for identifying a presence of a plurality of biomarkers in a biological sample of a subject, comprising: (a) performing a single assay on the biological sample to detect a plurality of biomarkers in the biological sample that is indicative of diabetes in the subject, which biological sample has a volume that is less than or equal to 50 microliters; and (b) identifying the presence of the plurality of biomarkers in the biological sample based on the single assay performed in (a).

In some embodiments of aspects provided herein, the method further comprises generating an electronic report that is indicative of the presence of the plurality of biomarkers in the biological sample. In some embodiments of aspects provided herein, the electronic report identifies a presence or absence of diabetes in the subject. In some embodiments of aspects provided herein, the method further comprises providing the electronic report for display on a user interface of an electronic device of a user. In some embodiments of aspects provided herein, the method further comprises providing a therapeutic intervention upon identifying the presence of the plurality of biomarkers in the subject. In some embodiments of aspects provided herein, the method further comprises performing an additional single assay on another biological sample of the subject. In some embodiments of aspects provided herein, the method further comprises monitoring a progression of diabetes in the subject based on the single assay and the additional single assay performed at separate time points. In some embodiments of aspects provided herein, the biological sample is a blood sample. In some embodiments of aspects provided herein, the volume is less than or equal to about 30 microliters. In some embodiments of aspects provided herein, the volume is less than or equal to about 20 microliters. In some embodiments of aspects provided herein, the volume is less than or equal to about 10 microliters. In some embodiments of aspects provided herein, the volume is less than or equal to about 5 microliters. In some embodiments of aspects provided herein, the volume is less than or equal to about 1 microliter. In some embodiments of aspects provided herein, the plurality of biomarkers includes any two of glycated hemoglobin (HbA1c), glycated albumin (GA) and glucose. In some embodiments of aspects provided herein, the plurality of biomarkers includes all of glycated hemoglobin (HbA1c), glycated albumin (GA) and glucose. In some embodiments of aspects provided herein, the glucose is fasting plasma glucose. In some embodiments of aspects provided herein, the plurality of biomarkers includes two or more biomarkers selected from the group consisting of HSA-Cys, HbA-SNO, GapoA-I and apoA-I MetO. In some embodiments of aspects provided herein, (a)-(b) are performed in a time period that is less than or equal to 1 hour. In some embodiments of aspects provided herein, the time period is less than or equal to 30 minutes. In some embodiments of aspects provided herein, the time period is less than or equal to 10 minutes. In some embodiments of aspects provided herein, the time period is less than or equal to 5 minutes. In some embodiments of aspects provided herein, the single assay is a microfluidic device that is operatively coupled to a mass spectrometer, and the performing comprises directing the biological sample from the microfluidic device to the mass spectrometer. In some embodiments of aspects provided herein, an individual biomarker in the biological sample is identified based on an ionization pattern of the individual biomarkers in the mass spectrometer. In some embodiments of aspects provided herein, the microfluidic device comprises a fluid channel in fluid communication with an emitter having a plurality of nozzles that are adapted to direct the biological sample or a portion thereof to the mass spectrometer. In some embodiments of aspects provided herein, the fluid channel includes a separation medium that is adapted to separate the plurality of biomarkers into a subset of biomarkers along the channel. In some embodiments of aspects provided herein, the separation medium includes beads. In some embodiments of aspects provided herein, the plurality of biomarkers is indicative of oxidative stress and/or cardiovascular risks of diabetes.

Another aspect of the present disclosure provides a method for identifying a presence of a plurality of biomarkers in a biological sample of a subject, comprising assaying the biological sample to identify the presence of the plurality of biomarkers in the biological sample having a volume that is less than or equal to about 50 microliters in a time period that is less than or equal to 1 hour and a specificity to the plurality of biomarkers that is at least about 80%, wherein the plurality of biomarkers is indicative of diabetes in the subject.

In some embodiments of aspects provided herein, the method further comprises generating an electronic report that is indicative of the presence of the plurality of biomarkers in the biological sample. In some embodiments of aspects provided herein, the electronic report identifies a presence or absence of diabetes in the subject. In some embodiments of aspects provided herein, the method further comprises providing a therapeutic intervention upon identifying the presence of the plurality of biomarkers in the subject. In some embodiments of aspects provided herein, the method further comprises monitoring a progression of diabetes based on sequential measurements of biological samples of the subject. In some embodiments of aspects provided herein, the biological sample is a blood sample. In some embodiments of aspects provided herein, the volume is less than or equal to about 30 microliters. In some embodiments of aspects provided herein, the volume is less than or equal to about 20 microliters. In some embodiments of aspects provided herein, the volume is less than or equal to about 10 microliters. In some embodiments of aspects provided herein, the volume is less than or equal to about 5 microliters. In some embodiments of aspects provided herein, the volume is less than or equal to about 1 microliter. In some embodiments of aspects provided herein, the plurality of biomarkers includes any two of glycated hemoglobin (HbA1c), glycated albumin (GA) and glucose. In some embodiments of aspects provided herein, the plurality of biomarkers includes all of glycated hemoglobin (HbA1c), glycated albumin (GA) and glucose. In some embodiments of aspects provided herein, the glucose is fasting plasma glucose. In some embodiments of aspects provided herein, the plurality of biomarkers includes two or more biomarkers selected from the group consisting of HSA-Cys, HbA-SNO, GapoA-I and apoA-I MetO. In some embodiments of aspects provided herein, the time period is less than or equal to 30 minutes. In some embodiments of aspects provided herein, the time period is less than or equal to 10 minutes. In some embodiments of aspects provided herein, the time period is less than or equal to 5 minutes. In some embodiments of aspects provided herein, the biological sample is assayed with a microfluidic device that is operatively coupled to a mass spectrometer, wherein the microfluidic device separates the plurality of biomarkers into individual biomarkers for detection by the mass spectrometer. In some embodiments of aspects provided herein, the microfluidic device includes beads that separate the plurality of biomarkers into the individual biomarkers. In some embodiments of aspects provided herein, the specificity is at least about 90%. In some embodiments of aspects provided herein, the specificity is at least about 95%. In some embodiments of aspects provided herein, the specificity is at least about 99%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIGS. 1a and 1b show an example microfluidic device and its assembly;

FIG. 6a shows an example calibration curve for the ratio of HbA1c:HbA determined by the assay for given molar ratios of the mixtures of purified HbA1c and HbA0. FIG. 6b shows comparison of HbA1c values for the Lyphochek® Hemoglobin A1c linearity set samples (LOT 34650), obtained by an example multinozzle emitter array (MEA) chip-based assay (x), and the corresponding target values using other commercial assays (NGSP (♦) and IFCC (○)). FIGS. 6c and 6d show a comparison of HbA1c values for blood samples from 8 Type 2 diabetes (T2D) patients, each measured by both an example MEA chip and a commercial Tosoh G7 HPLC analyzer, showing the correlation between the values obtained by the two methods (Pearson's correlation, r=0.9695, p<0.0001, n=8) and Bland-Altman plot of the difference between the two methods. The lines are plotted indicating the bias (0.80%) and the upper and lower limits of agreement (LoA) (bias±2×s.d.);

FIGS. 7a-7c show quantitation of the glycation levels of HbA (HbA1c), HSA (GA), and apoA-I (GapoA-I) in controls and Type 2 diabetes (T2D), respectively (n=8 for each group). The mean HbA1c, GA, and GapoA-I levels in T2D are 8.44%, 30.93%, and 5.10%, respectively, while in controls are 5.95%, 17.05%, and 3.63%, respectively. The p value is calculated using the two-tailed Student's t-test. FIGS. 7d-7f show correlation between any two values of HbA1c, GA, and GapoA-I, respectively, for each subject monitored (n=16, Pearson's correlation, p<0.0001);

FIGS. 8a-8c show comparison of the levels of HSA cysteinylation (HSA-Cys), hemoglobin nitrosylation (HbA-SNO), and apoA-I oxidation at 1-3 methionine residues (apoA-I MetO), between controls and T2D, respectively (n=8 for each group). The mean HSA-Cys, HbA-SNO, and apoA-I MetO levels in T2D are 49.59%, 19.33%, and 11.02%, respectively, while in controls are 36.96%, 20.17%, and 10.39%, respectively. The p value is calculated using the two-tailed Student's t-test. FIG. 8d shows correlation between the levels of HSA-Cys and GA (●), HbA1c (Δ), and GapoA-I (x), respectively, for each subject monitored (n=16, Pearson's correlation). FIG. 8e shows correlation between the age of T2D subjects and their levels of HSA-Cys (●), HbA-SNO (Δ), and apoA-I MetO (x), respectively (n=8, Pearson's correlation);

DETAILED DESCRIPTION

Figure 2:
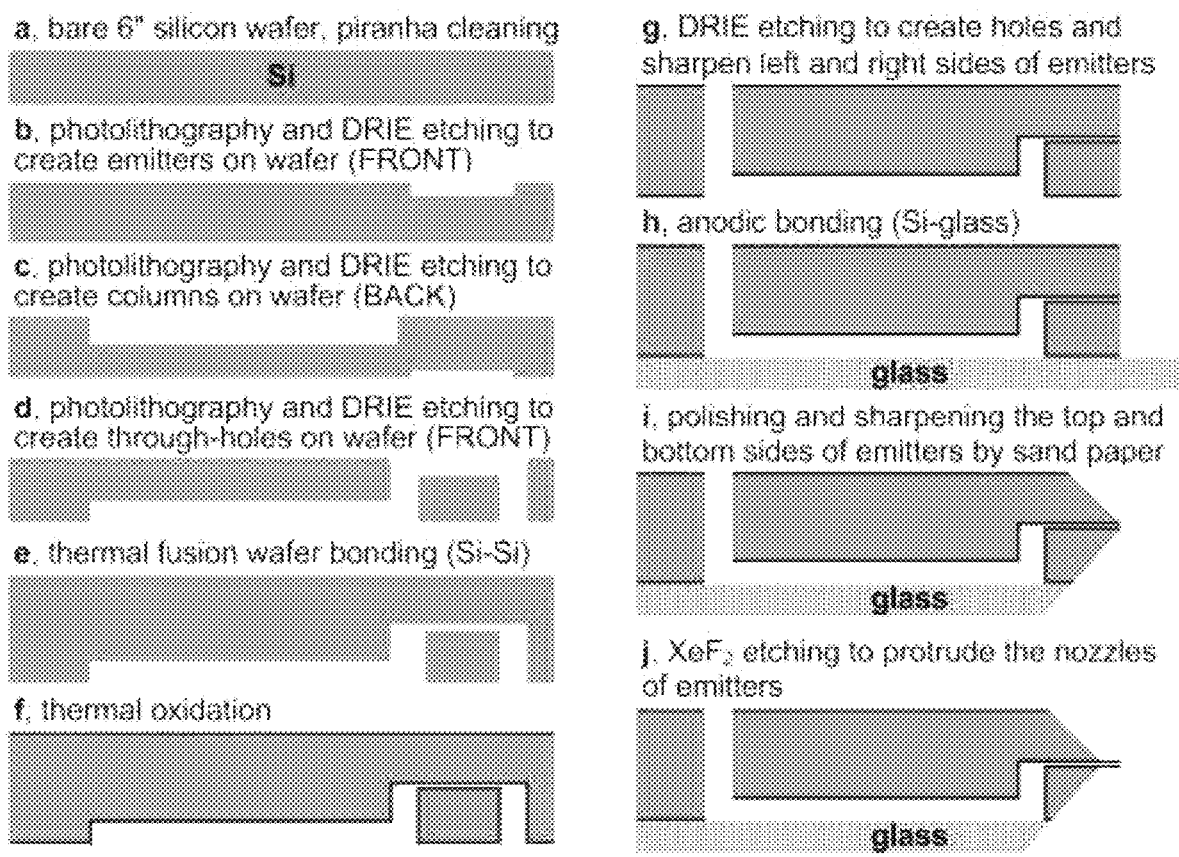
FIG. 2 illustrates the schematic of an example fabrication processes for the microfluidic device of FIGS. 1a and 1b.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "biomarker," as used herein, generally refers to any substances (e.g., composition and/or molecules), or a complex of substances, which is associated with a biological state or condition of an organism, such as a subject. Examples of such biological state or condition include, without limitation, a disease, a disorder, a non-disease condition, or therapeutic responses to different drug treatments and other therapies.

The term "subject," as used herein generally refers to any living being comprised of at least one cell. An organism can be a single cell organism or a multi-cellular organism, such as a mammal, a non-mammal (e.g., a bird), or a plant (e.g., a tree). An organism may be a mammal, such as, for example, a human or an animal such as a primate (e.g., a monkey, chimpanzee, etc.), a domesticated animal (e.g., a dog, cat, etc.), farm animal (e.g., goat, sheep, pig, cattle, horse, etc.), or laboratory animal (e.g., mouse, rat, etc.). A subject may be a patient. A subject may be an individual that has or is suspected of having a disease.

Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. The subject may be a normal healthy pregnant woman, or a pregnant woman who is at risk of carrying a baby with certain birth defect.

Overview

Mass Spectrometry (MS) is an analytical technique that can be used for identifying the amount and type of chemicals present in a sample, determining the elemental composition of samples, quantifying the mass of particles and molecules, and elucidating the chemical structure of molecules by measuring the mass-to-charge ratio and the abundance of gas-phase ions. Various types of MS-based technologies with high specificity, such as Liquid Chromatography (LC-MS), Gas Chromatography (GC-MS), and Matrix-Assisted Laser Desorption/Ionization/Time-Of-Flight (MALDI-TOF MS), can be utilized as tools in clinical laboratories for disease screening, diagnosis of disease and metabolic disorders, monitoring of drug therapy, identifying drug toxicity and poisoning, and discovering new biomarkers.

Mass spectrometry-based proteomics can be an indispensable and powerful tool for diagnostics of diseases and monitoring of their progression and therapeutic responses. The focus of clinical proteomics has been on analyzing low-abundance proteins using bottom-up proteomics (i.e., analysis of proteolytic peptides), which faces the challenge of the huge dynamic range in biological fluids such as blood and urine, and the difficulty of identifying all protein isoforms (or proteoforms), including splicing, modifications, cleavages etc., and quantifying their stoichiometry. There have been recent advances in top-down proteomics, i.e., large-scale identification and characterization of full-length proteins, but its clinical potentials remain largely unexplored. The ability of mass spectrometry to identify and, more importantly, to precisely quantify thousands of proteins from complex samples can be useful in the fields of biology and medicine.

The present disclosure provides methods and systems for detecting a presence or absence of one or more of substances (e.g., biomarkers) in a sample which is indicative of a biological state or a condition (e.g., a disease, a non-disease condition) in a subject. The presence or absence of one or more of the substances can be used for determining a risk of developing a disease, diagnosing a disease or monitoring a progression of a disease in a subject. In some cases, the presence or absence of the substances in the sample may further comprise determining a level (e.g., concentration, quantity and amount) for one or more of the substances and the determined level of the substances may be utilized to draw a conclusion. In some cases, the determined level of one or more of the substances may be compared to that in a control sample prior to making the diagnosis.

The systems provided herein may comprise (1) a detection module comprising at least one detector; (2) a microfluidic device comprising at least one fluid channel and at least one emitter; and (3) a computer control system that may control the operation of the microfluidic device, including flow, voltage, heating etc., as well as coupled to either or both of the detection module and the microfluidic device. Each part of the systems may be integrated with or separated from other parts of the systems. For example, in some cases, the detection module may be separated from the microfluidic device and the computer control system. In some cases, the detection module may be integrated with the microfluidic device, but separated from the computer control system. The microfluidic device may be integrated with the computer control system, while separated from the detection module. As an alternative, the microfluidic device may be separate from the computer control system.

In some examples, the system may comprise (1) a detector, which is adapted to generate signals that are indicative of a presence or absence of one or more of substances; (2) a microfluidic device including at least one fluid channel in fluidic communication with at least one emitter having at least one nozzle that is operatively coupled to the detector, wherein the fluid channel may include a separation medium that is adapted to separate the one or more of substances into subsets of substances along the fluid channel; and (3) a computer processor coupled to the microfluidic device and programmed to (i) direct a biological sample through the fluid channel to the at least one emitter under conditions that permit the one or more of substances to separate into the subsets of substances along the fluid channel; (ii) direct at least a portion of the sample from the at least one nozzle to the detector, wherein the detector may generate signals upon contact (e.g., direct contact) with the portion of the sample; and (iii) detect the presence or absence of the subsets of substances in the sample based on the signals generated in (ii) to detect a presence or absence of the one or more of substances in the sample. In some cases, the at least one emitter may include a plurality of emitters, such as at least 2, 3, 4, 5, 6, 7, 8, 9, 10, 20, 30, 40, or 50 or more emitters. The at least one nozzle may include a plurality of nozzles, such as at least 2, 3, 4, 5, 6, 7, 8, 9, 10, 20, 30, 40, 50, 100 or more nozzles per emitter.

In some examples, methods for detecting one or more substances in a sample may comprise steps of (a) providing a microfluidic device including at least one fluid channel in fluid communication with at least one emitter having at least one nozzle that is operatively coupled to a detector, wherein the fluid channel may include a separation medium that is adapted to separate the one or more of substances into subsets of substances along the fluid channel, and the detector is adapted to generate signals that are indicative of each of the subsets of substances; (b) directing the sample through the fluid channel to the at least one emitter under conditions that permit the one or more of substances to be separated into the subsets of substances along the fluid channel; (c) directing at least a portion of the sample from the at least one nozzle to the detector, wherein the detector may generate signals upon contact with the at least a portion of the sample; and (d) detecting a presence or absence of the subsets of substances based on the signals generated in step (c) to detect the presence or absence of the one or more of substances in the sample. As provided herein, the steps (a)-(d) may be performed with or without obtaining an immediate diagnostic result.

In an aspect of the present disclosure, fast-diagnostic methods may be provided. For example, time period as measured from the sample loading to MS detection or identification may be less than or equal to about 48 hours, 36 hours, 24 hours, 12 hours, 10 hours, 8 hours, 6 hours, 5 hours, 4 hours, 3 hours, 2 hours, 1 hour, 50 minute (min), 45 min, 40 min, 35 min, 30 min, 25 min, 20 min, 15 min, 10 min, 9 min, 8 min, 7 min, 6 min, 5 min, 4 min, 3 min, 2 min, 1 min, or less.

In some cases, the methods may further comprise generating an electronic report that is indicative of the presence or absence of the one or more of substances in the sample. The methods may further comprise providing the electronic report for display on a user interface (UI) of an electronic device of a user, such as a graphical user interface (GUI). A disease in a subject may be identified based on the presence or absence of the one or more of substances in the sample of the subject. In some cases, the methods may further comprise detecting the presence or absence of the subsets of substances at multiple time points to monitor a progression of a disease in a subject. The methods may also comprise providing a therapeutic intervention upon identifying the presence or absence of the one or more of substances in the sample.

Also provided in the present disclosure are methods and systems for identifying a presence or absence of one or more of substances in a sample of a subject, wherein the presence or absence of the one or more of substances may be indicative of a disease in the subject. The methods and systems may comprise (1) a detection module comprising at least one detector; (2) a microfluidic device comprising at least one fluid channel and at least one emitter; and (3) a computer control system coupled to either or both of the detection module and the microfluidic device. A sample of a subject may be assayed with the microfluidic device that is operatively coupled to the detector, wherein the microfluidic device may separate one or more of substances in the sample into individual or subsets of substances for detection by the detector.

In some examples, the methods may comprise (a) performing an assay (e.g., single assay, multiplex assay etc.) on the sample to detect one or more of substances in the sample that is indicative of a disease in the subject; and (b) identifying the presence or absence of the one or more of substances in the sample based on the assay performed in (a).

In some cases, the methods may further comprise generating an electronic report that is indicative of the presence or absence of the one or more of substances in the sample. In some cases, the electronic report may identify a presence or absence of a disease in the subject. In some cases, the methods may further comprise providing the electronic report for display on a user interface of an electronic device of a user. A therapeutic intervention may be provided upon identifying the presence or absence of the one or more of substances in the subject. The methods may further comprise monitoring a progression of a disease in the subject based on the assay performed in (a). In some cases, one or more of additional assays (e.g., single assay, multiplex assay etc.) may be performed on the sample of the subject. The one or more additional assays may be performed on the same sample or a different sample of the subject. The additional assays may be performed at the same time or multiple time points. Based upon the assay performed in (a) and the one or more additional assays performed, a presence or absence of a disease in the subject may be identified. Or, in some cases, the assay preformed in (a) and the one or more additional assays may be utilized to monitor the progression of a disease in the subject.

Further provided in the present disclosure are methods and systems for diagnosing a disease, determining the risk of developing a disease, monitoring the progression of a disease, and/or monitoring the therapeutic responses of a disease in a subject by measuring the concentration, quantity and/or amount of one or more substances in a substantially small amount (e.g., less than 5 microliters) of biological sample from the subject. The measured concentration, quantity and/or amount of one or more substances in the sample may or may not be compared with that in a control sample to make the diagnosis. For example, in some cases, an elevated or lowered amount of one or more substances in the sample of the subject may be indicative of a disease. In some cases, when compared with the control, the same level of one or more substances in the sample of the subject may signal the absence of a disease.

Microfluidic Device

The present disclosure also provides microfluidic devices for sample detection. A microfluidic device can include a set of micro-channels etched or molded into a material (e.g., glass, silicon or polymer etc.). The micro-channels forming the microfluidic device may be connected together in order to achieve a desired function (e.g., mix, pump, transport, direct, redirect and/or allow flow of a substance or a group of substances inside channels). In some cases, the microfluidic device may be a chip (e.g., a single-plex chip, a multi-plex chip). In some cases, the microfluidic device may be part of a chip. A chip may be assembled from a plurality of multiple multi-layer microfluidic devices using manifolds and clamps. The chip may have a feature of disposability or multi-uses. The microfluidic device may be disposable or reusable. For example, in some cases, the microfluidic device may be single use for a single sample or a plurality of samples. In some cases, the microfluidic device may be multi-use for a single sample or a plurality of samples.

Microfluidic devices provided herein may comprise more than one functional component, which can be used for e.g., sample processing and preparation, separation, and/or ionization. As described above and elsewhere herein, the microfluidic device may comprise at least one fluid channel that is in fluidic communication with at least one emitter. The emitter may have at least one nozzle.

The number of fluid channels and emitters included in the device may vary, depending upon, applications of the device. For example, a plurality of fluid channels may be preferred when multiple samples are to be analyzed in parallel. In some cases, a large number of fluid channels may be included in the device. In some cases, a small number of fluid channels may be included in the device. In some cases, the microfluidic device may comprise greater than or equal to about 1, 2, 3, 4, 5, 6, 7, 8, 9, 10, 15, 20, 25, 30, 35, 40, 50, 60, 70, 80, 90, 100, or more fluid channels. In some cases, the microfluidic device may comprise less than about 300, 250, 200, 150, 100, 90, 80, 70, 60, 50, 40, 30, 20, 15, 14, 13, 12, 11, 10, 9, 8, 7, 6, 5, 4, 3, 2, or 1 fluid channel. In some cases, the number of fluid channels included in the device may be between any of the two values described herein, for example, about 24.

As provided herein, at least one fluid channel may be used for sample separation, i.e., after sample is collected, processed or prepared, substances of interest included in the sample may be separated or fractionated by at least one fluid channel. The at least one fluid channel may be used to enrich the sample. In some cases, the sample may be prepared or processed before being directed into the fluid channel for sample separation. In some cases, sample preparation or processing may occur at a different location in the microfluidic device (e.g., in a separate fluid channel). In some cases, sample preparation or processing may take place at the same location in the microfluidic device (e.g., within the same fluid channel). In some cases, the microfluidic device may include a layered structure that monolithically integrates several functional modules (e.g., fluid channels) on a single device. Non-limiting examples of functional fluid channels may include sample loading channel (or sample input, sample inlet), extraction channel (or extraction segment), trap channel (or trap column), separation channel (or separation column), enrichment channel (i.e., channels adapted to fragment and/or concentrate the substances into subsets of the substances), sample exit channel (or sample outlet), or combinations thereof. Each of the fluid channels may be in fluid communication with one or more other fluid channels. For example, a microfluidic device may include a plurality of sample inputs and a fluid channel, wherein the plurality of sample inputs are in fluid communication with the fluid channel. The fluid channel may further comprise a separation channel and an enrichment channel with the separation channel being downstream of and in fluid communication with the enrichment channel. In some examples, a microfluidic device may comprise a sample inlet, a trap channel and a separation channel, wherein the trap channel is in fluid communication with both the sample inlet and the separation channel.

The fluid channel may be of different shapes, e.g., cube, cuboid, cone, cylinder, prism, pyramid, or any regular or irregular shapes. In cases where more than one fluid channels are comprised in the device, each of the fluid channels may be of the same or a different shape. In some cases, a certain percentage of the fluid channels may have the same or a different shape, for example, 99% of the fluid channels may have the same shape.

The length of the fluid channel may vary, depending upon, for example, quantity, acidity, basicity, charge, size, architecture, hydrophobicity, hydrophobicity, and affinity of the analyte. In some cases, a longer fluid channel may be preferred. In some cases, a shorter fluid channel may be used. In some cases, the length of the fluid channel may be less than or equal to about 100 centimeters (cm), 75 cm, 50 cm, 25 cm, 20 cm, 18 cm, 16 cm, 14 cm, 12 cm, 10 cm, 9 cm, 8 cm, 7 cm, 6 cm, 5 cm, 4 cm, 3 cm, 2 cm, 1 cm, 0.5 cm, 0.25 cm, 0.1 cm, 0.05 cm, or 0.01 cm. In some cases, the length of the fluid channel may be at least about 0.0001 cm, 0.0005 cm, 0.001 cm, 0.005 cm, 0.01 cm, 0.05 cm, 0.1 cm, 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 18 cm, 20 cm, 25 cm, 30 cm, 35 cm, 40 cm, 50 cm, 60 cm, 70 cm, 80 cm, 90 cm, 100 cm, 200 cm, or more. In some cases, the length of the channel may be between any of two values described herein.

In some cases, the fluid channel may have a cross-section that is of a certain shape, for example, square, triangular, rectangular, circular, polygonal, or any types of regular or random shapes. Dimensions of the cross-section of the fluid channel may vary. For example, the dimension for each side of the shape are less than or equal to about 5000 microns (μm), 4000 μm, 3000 μm, 2000 μm, 1000 μm, 750 μm, 500 μm, 450 μm, 400 μm, 350 μm, 300 μm, 250 μm, 200 μm, 190 μm, 180 μm, 170 μm, 160 μm, 150 μm, 140 μm, 130 μm, 120 μm, 110 μm, 100 μm, 90 μm, 80 μm, 70 μm, 50 μm, 30 μm, 10 μm, 5 μm, 1 μm, or less. In some cases, the dimension for each side of the shape are at least about 1 μm, 5 μm, 10 μm, 25 μm, 50 μm, 75 μm, 80 μm, 90 μm, 100 μm, 110 μm, 120 μm, 130 μm, 140 μm, 145 μm, 150 μm, 160 μm, 170 μm, 180 μm, 190 μm, 200 μm, 250 μm, 300 μm, 350 μm, 400 μm, 450 μm, 500 μm, 750 μm, 1000 μm, or more. In some cases, the dimension for each side of the shape may be between any of the two values described herein. In some examples, the fluid channel may have a cross-section of about 100 μm×100 μm. In some example, the fluid channel may have a cross-section of about 200 μm×200 μm. In some example, the fluid channel may have a cross-section of about 120 μm×300 μm.

As will be appreciated, in some cases, it may be preferred that each of the fluid channels has different dimensions. For example, a separation channel may be designed to be 5 cm×100 μm×100 μm, while the trap column is 1 cm×300 μm×120 μm. In some cases, each fluid channel in the microfluidic device may be of the same dimensions, for example, 4 cm×150 μm×150 μm. In some cases, it may be desired that a certain percentage of the fluid channels are of the same dimensions, e.g., about 5%, 10%, 15%, 20%, 25%, 30%, 35%, 40%, 50%, 60%, 70%, 80%, 90%, or 100% of the fluid channels.

Flow rates for the fluid channels may vary, dependent upon, for example, channel dimensions. For example, a fluid channel with smaller cross-sectional dimensions may require a lower flow rate. For example, a fluid channel with dimensions of 1 cm×300 μm×120 μm may be capable of a flow rate of about 20 microliters (μL)/minute (min), while a fluid channel with dimensions of 5 cm×100 μm×100 μm may only be capable of a flow rate of about 600 nanoliters (nL)/min.

Various methods or techniques may be used for sample separation. Non-limiting examples of methods or techniques may include Column Chromatography, Paper Chromatography, Thin Layer Chromatography, Gas Chromatography, Liquid Chromatography, Supercritical Fluid Chromatography, Ion Exchange Chromatography, Size-exclusion Chromatography, Expanded Bed Adsorption (EBA) Chromatographic Separation, Two-dimensional Chromatography, Simulated moving-bed Chromatography, Pyrolysis Gas Chromatography, Fast Protein Liquid Chromatography, Countercurrent Chromatography, Chiral Chromatography, Capillary Electrophoresis, Capillary Gel Electrophoresis, Capillary Zone Electrophoresis, Capillary Isoelectric Focusing, Capillary Electrochromatography, or combinations thereof. As provided herein, at least one fluid channel may be adapted to separate substances of interest included in a sample, based on one or more of the abovementioned separation techniques. For example, in some cases, the microfluidic device may comprise at least one fluid channel (or LC-column) to perform Liquid Chromatography on the sample.

In cases where at least one fluid channel is a LC-column, the column comprises a separation medium that is adapted to separate substances included in a sample into subsets of substances along the column when the sample is forced through the channel under high pressure. The separation medium may comprise porous monoliths directly fabricated inside the column, which can be porous rod structures characterized by mesopores and macropores. As an alternative or in addition to, the separation medium may comprise a plurality of particles (e.g., silica particles, polymer particles, sorbents, or beads) with the same or varying sizes, porosity, and functional groups for diverse liquid chromatography (LC) separation including, but not limited to, reverse-phase, ion-exchange, size-exclusion, and hydrophilic interaction liquid chromatography (HILIC). In some cases, all of the particles have the same size. In some cases, each of the particles may have a different size. In some cases, a certain portion of the particles may have the same size. Particle size (or dimensions) may vary, depending upon, for example, column length, separation time, resolution, detection limits, type of eluants used etc. In some cases, the particles may have a size (or cross-sectional dimension) greater than or equal to about 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 17 µm, 19 µm, 20 µm, 30 µm, 40 µm, 50 µm, 60 µm, 70 µm, 80 µm, 90 µm, 100 µm, or more. In some cases, the particle size (or cross-sectional dimension) may be less than or equal to about 300 µm, 200 µm, 150 µm, 100 µm, 90 µm, 80 µm, 70 µm, 60 µm, 50 µm, 40 µm, 30 µm, 25 µm, 20 µm, 18 µm, 16 µm, 14 µm, 12 µm, 10 µm, 8 µm, 7 µm, 6 µm, 5 µm, 4 µm, 3 µm, 2 µm, 1 µm, or less. In some cases, the particle size (or cross-sectional dimension) may be between any of the two values described herein. In some cases, the particles may have a narrow size distribution. In some cases, the particles may have a broad size distribution. For reverse-phase separation, the alkyl chains for the stationary phase may range from C1 (i.e., methyl), to C30, for example, C4, C8, or C18.

Various solvents may be used in LC-analysis, e.g., organic, inorganic, or mixed solvent. Non-limiting examples of solvents may include water, methanol, propanol, acetonitrile, dioxane, ethyl acetate, acetone, diethyl ether, tetrahydrofuran, methylene chloride, chloroform, carbon tetrachloride, isooctane, hexane, or combinations thereof. In some cases, solvent gradient may be required when running LC analysis. Gradients can be linear or non-linear. Gradients can have multiple segments. In some cases, it may be preferred to end the gradient at high organic, for example, 80-95%, since non-polar compounds may foul the column and decrease the resolution of the separation.

Microfluidic devices of the present disclosure can include one or more emitters. As described herein, the number of emitters comprised in each microfluidic device may vary. In some cases, a large number of emitters may be comprised in the microfluidic device. In some cases, a small number of emitters may be comprised in the device. In some cases, each microfluidic device may comprise greater than or equal to about 1, 2, 3, 4, 5, 6, 7, 8, 9, 10, 15, 20, 25, 30, 35, 40, 45, 50, 60, 70, 80, 90, 100, or more emitters. In some cases, each microfluidic device may comprise less than about 500, 400, 300, 200, 100, 90, 80, 70, 60, 50, 40, 30, 20, 15, 14, 13, 12, 11, 10, 9, 8, 7, 6, 5, 4, 3, 2, or 1 emitter. In some cases, the number of emitters comprised in each microfluidic device may be between any of the two values described herein, for example, about 24, or 96.

The emitter may further comprise at least one base tube (or base channel) and at least one nozzle, wherein the base tube is in fluidic communication with both the nozzle and at least one fluid channel. In some cases, the base tube may have the same cross-sectional dimension as the nozzle. In some cases, the base tube may have a larger cross-sectional dimension than the nozzle. In some cases, each emitter may comprise equal numbers of base tubes and nozzles, wherein each base tube is in fluid communication with each of the nozzles. In some cases, each emitter may comprise different numbers of base tubes and nozzles, and more than one of the base tubes (or nozzles) may be in fluid communication with each of the nozzles (or base tubes).

In some cases, each emitter may comprise at least about 1, 2, 3, 4, 5, 6, 7, 8, 9, 10, 15, 20, 25, 30, 35, 40, 45, 50, 60, 70, 80, 90, 100, or more base tubes. In some cases, each emitter may comprise less than or equal to about 300, 250, 200, 150, 100, 90, 80, 70, 60, 50, 40, 30, 20, 15, 14, 13, 12, 11, 10, 9, 8, 7, 6, 5, 4, 3, 2, or 1 base tubes. In some cases, the number of base tubes comprised in each emitter may fall between any of the two values described herein, for example, 12, or 14.

In some cases, each emitter may comprise at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500 or more nozzles. In some cases, each emitter may comprise less than or equal to about 1000, 900, 800, 700, 600, 500, 400, 300, 200, 100, 90, 80, 70, 60, 50, 45, 40, 35, 30, 25, 20, 19, 18, 17, 16, 15, 14, 15, 14, 13, 12, 11, 10, 9, 8, 7, 6, 5, 4, 3, 2, or 1 nozzle.

In some cases, the base tube and the nozzle are integrated with each other, for example, the walls of the nozzle and the base tube may form a monolithic whole. The base tube may be separated from the nozzle. In some cases, the nozzle may extend out from the base tube and the protruding length may vary. In cases where multiple nozzles are comprised in the emitter, each of the nozzles may have the same or a different protruding length. In some cases, a certain percentage of the nozzles may have the same or a different protruding length. In some cases, at least about 1%, 5%, 10%, 15%, 20%, 30%, 40%, 50%, 60%, 70%, 75%, 80%, 85%, 90%, 91%, 92%, 93%, 94%, 95%, 96%, 97%, 98%, 99%, or 100% of the nozzles may have the same or a different protruding length. In some cases, less than or equal to about 100%, 90%, 80%, 70%, 60%, 50%, 40%, 30%, 20%, 10%, 5%, or 1% of the nozzles may have the same or a different protruding length.

The protruding length of the nozzle may vary. In some cases, a longer length may be preferred. In some cases, a shorter length may be utilized. In some cases, the protruding length may be less than or equal to about 5000 µm, 4000 µm, 3000 µm, 2000 µm, 1000 µm, 750 µm, 500 µm, 400 µm, 300 µm, 250 µm, 200 µm, 190 µm, 180 µm, 170 µm, 160 µm, 150 µm, 140 µm, 130 µm, 120 µm, 110 µm, 100 µm, 90 µm, 80 µm, 70 µm, 60 µm, 50 µm, 40 µm, 30 µm, 20 µm, 10 µm, 5 µm, 1 µm, or less. In some cases, the protruding length of the nozzle may be greater than or equal to about 1 µm, 5 µm, 10 µm, 20 µm, 30 µm, 40 µm, 50 µm, 60 µm, 70 µm, 80 µm, 90 µm, 100 µm, 105 µm, 100 µm, 115 µm, 120 µm, 125 µm, 130 µm, 135 µm, 140 µm, 145 µm, 150 µm, 155 µm, 160 µm, 170 µm, 180 µm, 190 µm, 200 µm, 300 µm, 400 µm, 500 µm, 750 µm, 1000 µm or more. In some cases, the protruding length may be between any of the two values described herein, for example, about 99 µm.

In some cases, each nozzle may have a first end and a second end, wherein the first end may be seamlessly connected with the emitter, and the second end may comprise an aperture or opening. As provided herein, the aperture or opening of the nozzle may have a cross-section that can be of various shapes, for example, square, triangular, rectangular, circular, polygonal, or any types of regular or random shapes. In some cases, the nozzle can be a nanotube. In some cases, the nozzle can be a microtube.

In some cases, the aperture or opening of the nozzle may have a cross-section that is a square or essentially square shape and the length of each side of the shape may be less than or equal to about 500 µm, 400 µm, 300 µm, 200 µm, 150 µm, 100 µm, 90 µm, 80 µm, 70 µm, 60 µm, 50 µm, 45 µm, 40 µm, 35 µm, 30 µm, 29 µm, 28 µm, 27 µm, 26 µm, 25 µm, 24 µm, 23 µm, 22 µm, 21 µm, 20 µm, 18 µm, 16 µm, 14 µm, 12 µm, 10 µm, 8 µm, 6 µm, 4 µm, 2 µm, 1 µm, 0.5 µm, 0.1 µm, 0.05 µm, 0.01 µm, or less. In some cases, the length of each side of the shape may be at least about 0.0001 µm, 0.0005 µm, 0.001 µm, 0.005 µm, 0.01 µm, 0.05 µm, 0.1 µm, 0.5 µm, 1 µm, 3 µm, 5 µm, 7 µm, 9 µm, 10 µm, 12 µm, 14 µm, 16 µm, 18 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 40 µm, 45 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm or more. In some cases, the length of each side of the shape may fall between any of the two values described herein, for example, about 17 µm.

In some cases, the aperture or opening of the nozzle may have a cross-section that is of a circular or essentially circular shape and the diameter of the shape may vary. In some cases, the diameter of the shape may be less than or equal to about 500 µm, 400 µm, 300 µm, 200 µm, 150 µm, 100 µm, 90 µm, 80 µm, 70 µm, 60 µm, 50 µm, 45 µm, 40 µm, 35 µm, 30 µm, 29 µm, 28 µm, 27 µm, 26 µm, 25 µm, 24 µm, 23 µm, 22 µm, 21 µm, 20 µm, 18 µm, 16 µm, 14 µm, 12 µm, 10 µm, 8 µm, 6 µm, 4 µm, 2 µm, 1 µm, 0.5 µm, 0.1 µm, 0.05 µm, 0.01 µm or less. In some cases, the diameter of the shape may be at least about 0.0001 µm, 0.0005 µm, 0.001 µm, 0.005 µm, 0.01 µm, 0.05 µm, 0.1 µm, 0.5 µm, 1 µm, 3 µm, 5 µm, 7 µm, 9 µm, 10 µm, 12 µm, 14 µm, 16 µm, 18 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 40 µm, 45 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm or more. In some cases, the diameter of the shape may fall between any of the two values described herein, for example, about 41 µm.

In some cases, the aperture or opening of the nozzle may have a cross-section with a longest linear dimension less than or equal to about 500 µm, 400 µm, 300 µm, 200 µm, 150 µm, 100 µm, 90 µm, 80 µm, 70 µm, 60 µm, 50 µm, 45 µm, 40 µm, 35 µm, 30 µm, 29 µm, 28 µm, 27 µm, 26 µm, 25 µm, 24 µm, 23 µm, 22 µm, 21 µm, 20 µm, 18 µm, 16 µm, 14 µm, 12 µm, 10 µm, 8 µm, 6 µm, 4 µm, 2 µm, 1 µm, 0.5 µm, 0.1 µm, 0.05 µm, 0.01 µm or less. In some cases, the aperture or opening of the nozzle may have a cross-section with a longest linear dimension greater than or equal to about 0.0001 µm, 0.0005 µm, 0.001 µm, 0.005 µm, 0.01 µm, 0.05 µm, 0.1 µm, 0.5 µm, 1 µm, 3 µm, 5 µm, 7 µm, 9 µm, 10 µm, 12 µm, 14 µm, 16 µm, 18 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 40 µm, 45 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm or more. In some cases, the longest linear dimension of the cross-section of the nozzle may be between any of the two values described herein, for example, about 36 µm.

Also provided in the present disclosure is that the nozzle may be sharpened. In some cases, all of the nozzles comprised in the device may be sharpened. In some cases, a certain percentage of the nozzles may be sharpened, for example, about 1%, 5%, 10%, 20%, 30%, 40%, 50%, 60%, 70%, 80%, 90%, 95%, 99%, or 100% of the nozzles may be sharpened. In cases where the nozzle comprises more than one side, sharpening may occur on any side of the nozzle, for example, the nozzle may be one-sided sharpened, two-sided sharpened, three-sided sharpened, four-sided sharpened, or multiple-sided sharpened. In some cases, it may be preferred that none of the sides of the nozzle is sharpened, i.e., a flat-end nozzle. In some cases, the degrees of sharpening angles vary on any side of a nozzle or on any of the nozzles within a plurality of nozzles.

Flow rate at the emitter or the nozzle may vary, depending upon, for example, dimensions of the emitter or the nozzle, numbers of the emitter or the nozzle, or material used to fabricate the emitter or the nozzle. In some cases, the emitter or the nozzle may be capable of a flow rate of less than or equal to about 2000 nL/min, 1500 nL/min, 1000 nL/min, 900 nL/min, 800 nL/min, 700 nL/min, 600 nL/min, 500 nL/min, 400 nL/min, 300 nL/min, 200 nL/min, 100 nL/min, 90 nL/min, 80 nL/min, 70 nL/min, 60 nL/min, 50 nL/min, 40 nL/min, 30 nL/min, 20 nL/min, 10 nL/min, 5 nL/min, 4 nL/min, 3 nL/min, 2 nL/min, 1 nL/min, 0.8 nL/min, 0.6 nL/min, 0.4 nL/min, 0.2 nL/min, 0.1 nL/min, 0.05 nL/min, 0.01 nL/min, 0.005 nL/min, 0.001 nL/min or less. In some cases, the emitter or the nozzle may be capable of a flow rate greater than or equal to about 0 nL/min, 0.1 nL/min, 0.5 nL/min, 0.75 nL/min, 1 nL/min, 1.5 nL/min, 2 nL/min, 3 nL/min, 4 nL/min, 5 nL/min, 6 nL/min, 8 nL/min, 10 nL/min, 20 nL/min, 30 nL/min, 40 nL/min, 50 nL/min, 60 nL/min, 70 nL/min, 80 nL/min, 90 nL/min, 100 nL/min, 200 nL/min, 300 nL/min, 400 nL/min, 500 nL/min, 600 nL/min, 800 nL/min, 1000 nL/min, 2000 nL/min, 3000 nL/min, 4000 nL/min, 5000 nL/min or more. In some cases, the emitter or the nozzle may be capable of a flow rate falling between any of the two values described herein, for example, about 65 nL/min.

As described above and elsewhere in the present disclosure, each of the emitter or nozzle may be in fluid communication with a base tube (or channel). In some cases, the base tube (or channel) is a fluid channel. In some cases, the microfluidic device may further comprise a through-hole which is in fluid communication with the base tube. In some cases, the through-hole may be at an angle, such as perpendicular, relative to the base tube. In some cases, the microfluidic device may further comprise a tubing in fluid communication with the through-hole. The tubing can be made of various materials, for example, flexible, semi-rigid or rigid material. In some cases, the tubing may comprise a polymer, such as polytetrafluoroethylene (PTFE).

In some cases, the microfluidic device may comprise a multinozzle emitter array (MEA) chip. For example, the emitter may be a 1-, 5-, 10-, 20-, 30-, 40-, 50-, 60-, 70-, 80-, 90-, or 100-nozzle emitter. Each emitter may be in fluid communication with a through-hole of the chip for sample injection. Each through-hole may be in fluid communication with a fluid channel of about 100 µm in width and 100 µm in depth. In some cases, the multinozzle emitter may comprise sharpened features.

In cases where a LC-channel (or column) is included in the device, to retain the separation medium (e.g., particles) inside the LC-channel, at least one frit may be implemented between the LC-channel and the nozzle. In some cases, it may be preferred that the opening of the frit is smaller than the sizes of the constituents of the separation medium. In some cases, dimensions of an opening of the frit (e.g., diameter of the opening of the frit) may be about 1 nm to 100 µm, for example, about 100 nm, 500 nm, 1 µm, 3 µm, 5 µm, 10 µm, 25 µm, or 50 µm. In some cases, the back-end LC-channel may be sealed by fabricating sol-gel frits. In some cases, the back-end frits may be created by sol-gel process using direct heat or UV polymerization.

The design, fabrication, structure, and applications of microfluidic device may be as described in, for example, U.S. Pat. Nos. 8,022,361, 9,793,477, and PCT Patent Publication No. WO 2014/093080, each of which is incorporated herein by reference in its entirety.

Various methods or approaches may be utilized to fabricate the microfluidic device provided herein, such as etching, machining, cutting, molding, casting or embossing. As described elsewhere herein, it may be preferred to have a microfluidic device that can monolithically integrate several functional modules on a single chip. For example, a microfluidic device has at least one fluid channel in fluidic communication with at least one emitter, wherein the emitter further comprises at least a base tube and a plurality of nozzles seamlessly connected to the base tube.

As provided in the present disclosure, the microfluidic device may be manufactured by using different types of materials. Non-limiting examples of materials that can be utilized to fabricate the microfluidic device may include polymer (e.g., polydimethylsiloxane (PDMS), parylene, poly(methyl methacrylate) (PMMA), negative photoresist SU-8 etc.), silicon, silica, silicon-based material (e.g., silicon nitride), metal (e.g., titanium), glass, ceramic, paper, hydrogel, thermosets, elastomers, plastics, thermoplastics, or combinations thereof. Materials may be opaque, transparent, or translucent. Materials used to fabricate the device can be of any size. For example, a 1-inch, 2-inch, 4-inch, 6-inch, 8-inch, or 10-inch silicon wafer may be used.

For device fabrication, various processing steps may comprise, for example, deposition, removal, patterning, and modification of device properties. Deposition may comprise any process that grows, coats, or otherwise transfers a material onto the wafer. Exemplary technologies may include physical vapor deposition (PVD), chemical vapor deposition (CVD), electrochemical deposition (ECD), molecular beam epitaxy (MBE), atomic layer deposition (ALD), or combinations thereof. Removal may comprise any process that removes material from the wafer. Examples may include etch processes (either wet or dry) and chemical-mechanical planarization (CMP). Patterning is the shaping or altering of deposited materials, and is generally referred to as lithography. Exemplary procedures for patterning may comprise (i) coating the wafer with a chemical called a photoresist; (ii) exposing select portions of the wafer to short wavelength light; and (iii) washing away the exposed regions by a developer solution. After etching or other processing, the remaining photoresist is removed by plasma ashing. In some cases, the wafer is etched to produce trenches with a specified depth by deep reactive ion etching (DRIE).

In some cases, the microfluidic device may be manufactured via a "bottom-up" approach, which may comprise (i) growing silicon nanostructures onto a clean silicon surface of a silicon base segment with the other surfaces of the base segment coated with silica; (ii) oxidizing the grown silicon nanostructures; (iii) removing the silica from the distal ends of the base segment and the silicon nanostructures to expose silicon; and (iv) removing silicon from the interior of the structure to form an emitter.

In some cases, a "top-down" approach may be applied for fabricating the microfluidic device. As described herein, this approach may comprise steps of (i) etching a trench into the surface of a silicon substrate; (ii) sealing a silicon wafer onto the surface of the substrate, thus enclosing the trench to form a channel; (iii) cutting the two channel ends; (iv) oxidizing structure; (v) cutting one end of the structure to expose the silicon core structure; and (vi) removing a portion of the silicon core to form an emitter.

A fabricated device may comprise one or more substrates which may be made of the same or different materials, such a material or a combination of materials selected from metals, semiconductors and polymeric materials (e.g., plastics). In some examples, the fabricated device is formed of glass, silicon, a silicon-based material (e.g., silicon nitride or silica), a metal, paper, hydrogel, thermoset, elastomer, or thermoplastic. For example, the microfluidic device may comprise a first substrate and a second substrate, wherein the first substrate the second substrate may be formed of different materials (e.g., silicon and silicon oxide respectively). In some cases, the microfluidic device may comprise three substrates, wherein the first two layers may be made of a certain material and the third layer may be made of a different material. In some cases, each substrate comprised in the microfluidic device may have at least one layer. A fabricated device may comprise a single layer or multiple layers. For multiple layers, different layers of substrate may be permanently bonded (e.g., silicon-glass anodic bonding) or reversibly bonded. For reversible bonding, sealing between different layers may be achieved by clamping. In cases where the device comprises more than one layer, materials used to fabricate each layer may be the same or different. In between each of the two layers, a certain number of functional components may be disposed. For example, the microfluidic device may be fabricated from two layers, both of which are made of silicon wafers. A plurality of fluid channels and an emitter may be disposed between the first and the second silicon wafers. In some examples, the microfluidic device may comprise three layers, such as a first silicon layer, a second silicon layer and a glass layer. The first layer may define a sample input hole. The first and the second layer may define an exit channel having a first end and a second end. The emitter may be disposed between the first and the second layer. The second end of the exit channel may be proximate and in fluid communication with the emitter. The second layer and the glass layer may define a separation channel having a first end and a second end. The first end of the separation channel may be proximate and in fluid communication with the sample input hole, and the second end of the separation channel may be proximate and in fluid communication with the exit channel. The separation channel may be configured to contain media (e.g., separation media) and adapted to separate substances of interest included in the sample into subsets of substances. In some cases, the glass layer may be configured to monitor the on-chip processes (such as bead packing, sample separation or sample imaging) in real-time.

Figure 12A:
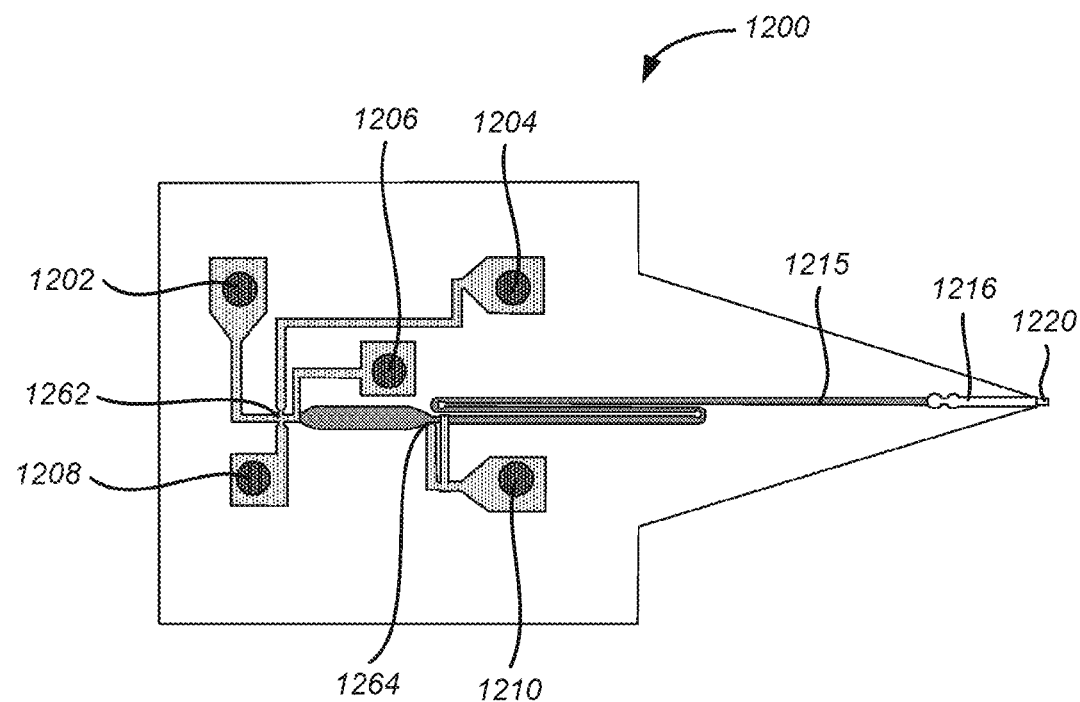
FIGS. 12a-12h schematically illustrate an example microfluidic device.
Figure 12B:
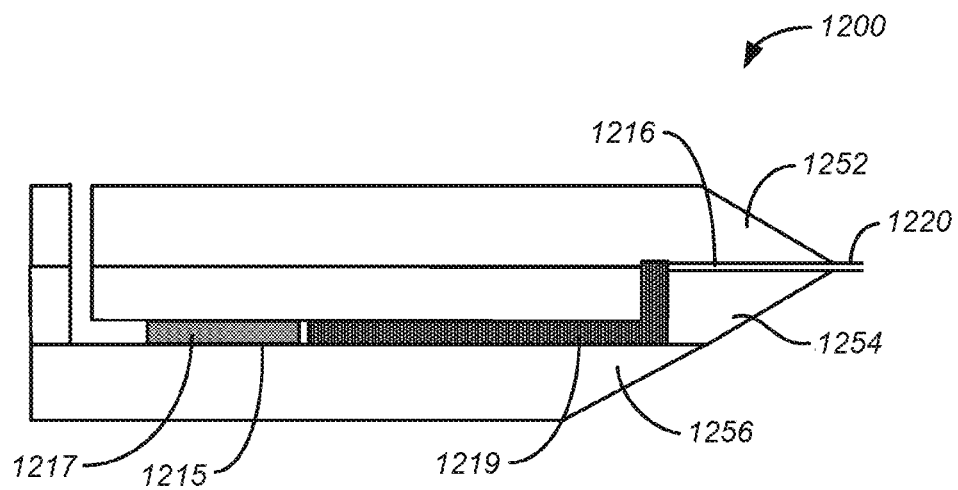

FIGS. 12a-12h show schematic illustrations and photographs of an example microfluidic device. FIG. 12a shows an example of a top-down schematic illustration of the device. FIG. 12b shows an example of a cross-sectional schematic illustration of a channel of the device. As described elsewhere herein, the device may include at least one fluid channel (e.g., a sample inlet, a separation channel etc.) and an emitter.

Detailed structure of the device is shown in FIGS. 12a and 12b, a microfluidic device 1200 may include a fluid channel. The fluid channel may further comprise a plurality of sample inputs 1202, 1204, 1206, and 1208, a processing channel 1215, an exit channel 1216, and an emitter 1220. A first end of the processing channel 1215 may be proximate and in fluid communication with the sample inputs 1202, 1204, 1206, and 1208. The sample inputs can be used to inject individual samples onto the device for separation and analysis. A second end of the processing channel 1215 may be proximate and in fluid communication with a first end of an exit channel 1216. A second end of the exit channel 1216 may be proximate and in fluid communication with an emitter 1220. By the elements of the channel being in fluid communication or connected with one another, a liquid sample may be introduced into the channel through a sample input, flowing through the processing channel 1215 and the exit channel 1216, and exit the device 1200 through the emitter 1220. The emitter 1220 may be used for electrospray MS identification and quantitation of one or more substances such as proteins and peptides, for example.

The fabricated device 1200 may comprise three wafers, a first wafer 1252, a second wafer 1254, and a transparent wafer 1256. In some cases, the first wafer 1252 and the second wafer 1254 may comprise silicon wafers. In some cases, the first wafer 1252 and the second wafer 1254 may comprise semiconductor wafers or other materials capable of conducting electricity. The emitter 1220 may be disposed between the first wafer 1252 and the second wafer 1254, and the transparent wafer 1256 may comprise a glass wafer or a portion of a sheet of glass. The transparent wafer 1256 may provide an imaging window that allows for real-time monitoring of on-line manipulation and processing of bead-packing in the column, as well as samples injection through the sample inputs 1202, 1204, 1206, and 1208.

In some cases, the processing channel 1215 may include an enrichment channel 1217 and a separation channel 1219. The enrichment channel 1217 and the separation channel 1219 may be configured to contain media (e.g., ZORBAX SB-C18 5 micron beads). The media may be used for separating the substances if one or more substances are included in the sample. In some cases, the media may be used for sample processing, for example, for protein enrichment and digestion, followed by peptide separation through on-line separation (e.g., liquid chromatography (LC)).

In some cases, the channel may be connected to an access hole 1210. The access hole 1210 may be used to fill the channel with media. For example, when the media include particles of beads, the media may be mixed with a liquid (e.g., an organic solvent, an inorganic solvent) and then forced into the channel though the access hole 1210 by using a pressurized gas (e.g., pressurized helium at about 250 psi) or a pump.

In some cases, the device 1200 may further include a plurality of frits 1264. The plurality of frits 1264 may be configured to retain the media in the processing channel 1215. In cases where cells are included in the sample, the device 1200 may further include a cell trap 1262. The cell trap 1262 may be used for capturing cells of interest with high specificity and sensitivity. A cell trap may include obstacles with inter-obstacle distances smaller than a cell. For example, a micropillar array with inter-pillar distance smaller than a cell can be used for a cell trap. Alternatively, a cell trap may include a filter or a plurality of filters with open pore sizes smaller than a cell.

Figure 12C:
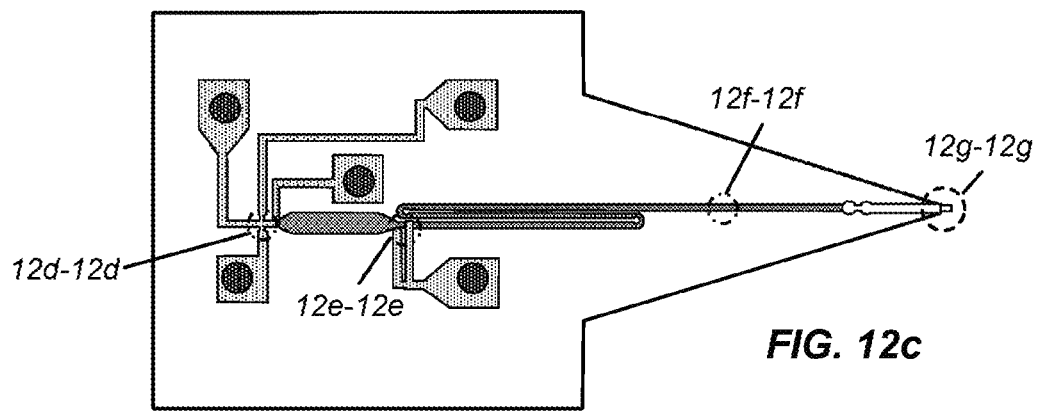
Figure 12D:
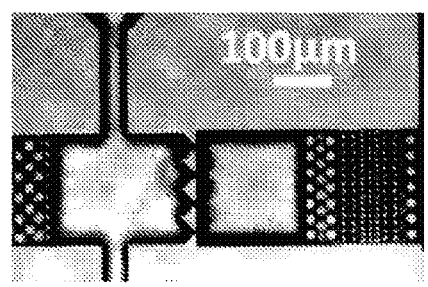
Figure 12E:
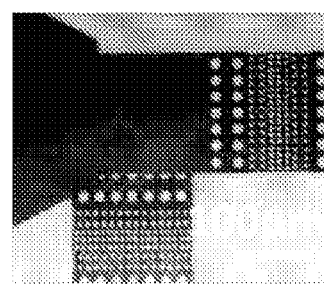
Figure 12F:
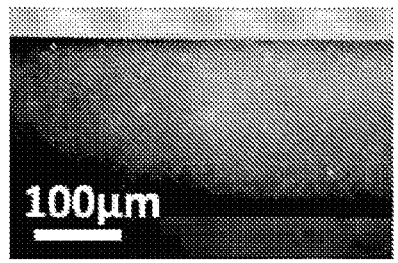
Figure 12G:
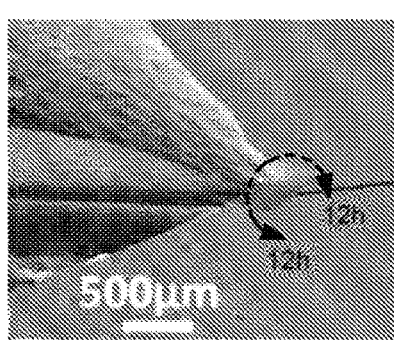
Figure 12H:
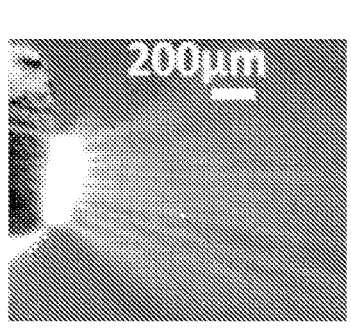

FIG. 12c shows an example of a schematic illustration of a fabricated device, with enlarged photographs of portions of the device including the cell trap (FIG. 12d), frits for channel packing with media (FIG. 12e), the media-packed processing channel (FIG. 12f), and the emitter (e.g., a multi-nozzle emitter) (FIGS. 12g and 12h). The multi-nozzle emitter shown in FIGS. 12g and 12h includes 10 nozzles, each with an inner diameter of about 10 microns, before and during electrospray. Other multi-nozzle emitter configurations are possible. The dimensions of the enrichment channel and the separation channel (width×depth×length) shown in FIG. 12c are about 1000 microns×100 microns×0.5 cm and about 200 microns×100 microns×4.5 cm, respectively. In some cases, dimensions for other components are specified with scale bars. As discussed elsewhere in the present disclosure, other dimensions of the enrichment and separation channels and other features of a microfluidic device are possible.

To establish a robust and high-quality fluidic connection to sustain high pressure for on-chip and online sample separation, a manifold may be utilized to mechanically assemble the device with capillary tubing connected to the outside flow source. The device may be sandwiched between a PEEK clamping plate and an aluminum plate, and tightly clamped by screws with O-rings in-between to prevent the fluid leakage. The top PEEK plate may have a plurality of threaded ports for Upchurch fittings to provide connections with capillary tubing. The assembly may then be fastened to a translational stage, using a screw in the aluminum plate. High voltage may be supplied to the device via the conductive aluminum plate. In some examples, no fluid leakage can be observed for the assembly for the flow under a pressure of over 2000 psi in LC-MS runs.

As described elsewhere herein, the present disclosure provides systems for detecting or identifying a presence or absence of one or more of substances (e.g., biomarkers, including cells, proteins, peptides, small molecules, etc.) in a sample of a subject. The detection of the presence or absence of one or more substances may further comprise detecting a presence or absence of one or more subsets of the substances. The substances or the subsets of the substances may be detected by various methods or techniques. The presence or absence of the one or more substances in the sample may be indicative of a disease of the subject. The systems may comprise a detection module, a microfluidic device and a computer control system. The detection module may comprise a single detector or a plurality of detectors. Non-limiting examples of detectors may include Flame ionization detector (FID), Aerosol-based detector (NQA), Flame photometric detector (FPD), Atomic-emission detector (AED), Nitrogen Phosphorus Detector (NPD), Evaporative light scattering detector (ELSD), Mass spectrometer (MS) (e.g., quadrupole MS, orthogonal MS etc.), UV detectors (e.g., diode array detector (DAD or PDA)), Thermal conductivity detector (TCD), Fluorescence detector, Electron capture detector (ECD), Conductivity monitor, Photoionization detector (PID), Refractive index detector (RI or RID), Radio flow detector, Chiral detector, or combinations thereof. Examples of detectors that may be used with methods and systems of the present disclosure are found in U.S. Pat. Nos. 8,022,361, 9,793,477, and PCT Patent Publication No. WO 2014/093080, each of which is incorporated herein by reference in its entirety.

In cases where a MS detector is utilized, the presence or absence of the substances or the subsets of the substances may be detected based on their ionization patterns in the mass spectrometer. The microfluidic device may be configured or adapted to direct at least a portion of the sample via the nozzle to the detector. Electrospray ionization (ESI) is a technique used in mass spectrometry to produce ions. It is especially useful in producing ions from macromolecules (such as proteins) because it overcomes the propensity of these molecules to fragment when ionized. The ions are accelerated under vacuum in an electric filed and separated by mass analyzers according to their m/z ratios. Exemplary mass analyzers include triple-quadrupole, time-of-flight (TOF), magnetic sector, orbitrap, ion trap, quadrupole-TOF, and Fourier transform ion cyclotron resonance (FTICR) analyzers etc. As individual ions reach the detector, they are counted.

For example, according to the structure of the device, materials used to fabricate the device, numbers, shapes and dimensions of fluid channels, emitters, and/or nozzles, the voltage applied onto the device (e.g., at the nozzle tip) may vary. In some cases, a high voltage may be required. In some cases, a low voltage may be used. In some cases, the voltage may fall into a range, for example, from about 0.1 kV to about 10 kV.

Moreover, as provided herein, the microfluidic device having sharpened-ended emitters (or emitters comprising sharpened nozzles) with a large number of nozzles (e.g., more than 40) per emitter may enable high-sensitivity MS detections. For example, the sensitivity may be greater than or equal to about 1.5×, 2×, 3×, 5×, 6×, 7×, 8×, 9×, 10×, 15×, 20× folds and more of those using the conventional electrospray MS through capillary emitters. With methods and systems provided in present disclosure, the specificity of the MS detection can be very high, for example, greater than or equal to about 50%, 60%, 70%, 75%, 80%, 85%, 90%, 91%, 92%, 93%, 94%, 95%, 96%, 97%, 98%, 99%, or 100%.

Also provided herein are methods of manufacturing multiplex chips for assay multiplexing. Two approaches may be utilized to implement the multiplex chips. (1) The multiplex chips may be built on silicon wafers as a whole complete piece, to facilitate simpler fabrication and lower cost. Examples of the 24-plex MEA chips containing multiplex LC-MS modules on a single monolithic devices can be seen in U.S. Pat. Nos. 8,022,361, 9,793,477, and PCT Patent Publication No. WO 2014/093080, each of which is incorporated herein by reference in its entirety. (2) The multiplex chips may be assembled using parallel 1-plex units. The approach may be used to create mass production on a large wafer and dice it into individual units (i.e., 1-plex chips). After passing QC, multiple 1-plex chips may be reconstituted to a multi-plex chip by assembly or packaging methods. This approach may allow better QC and much higher device yield, ensuring high reproducibility of inter- and intra-chip performance. With this approach, the units can be readily replaced with certified ones after long-term LC-MS operations. Both aforementioned multiplex chips can be used for multiplex assays of: (1) the same class of analytes from a plurality of samples obtained from the same or different subjects; and (2) different classes of analytes from samples obtained from the same or different subjects.

Computer Control System

Figure 11:
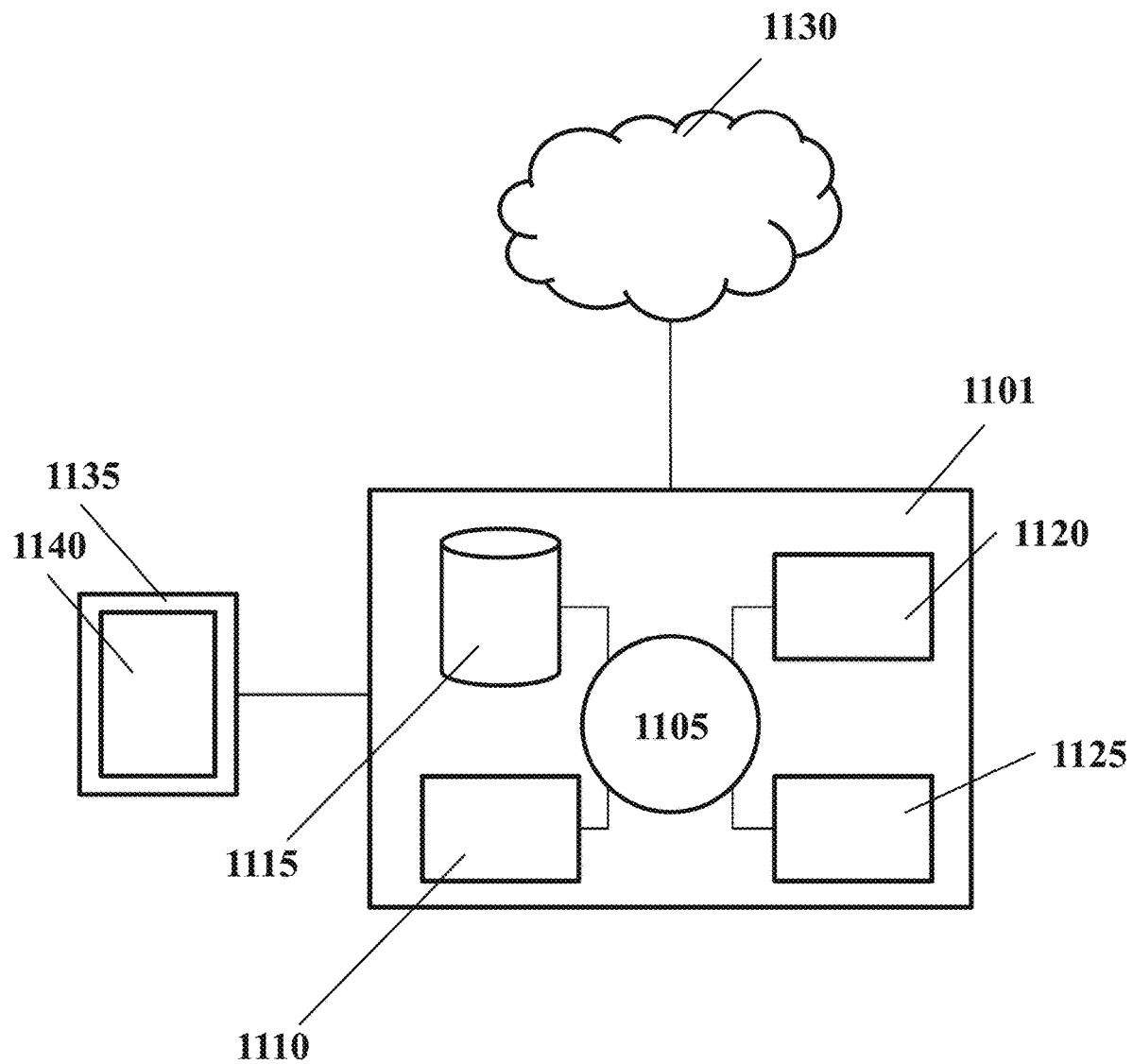
FIG. 11 shows a computer control system that is programmed or otherwise configured to implement methods provided herein.

The present disclosure provides computer control system that is programmed to implement methods of the disclosure. FIG. 11 shows a computer system 1101 that is programmed or otherwise configured to facilitate microfluidic chip operation, sample collection, preparation, processing, loading, separation, detection, and/or data analysis. The computer system 1101 can regulate various aspects of sample collection, preparation, processing, loading, separation and/or detection of the present disclosure, such as, for example, loading a sample into the microfluidic device, directing the sample through the fluid channels in the device for sample separation, directing the separated sample from the microfluidic device to the detection module. The computer system 1101 can be intergraded with the systems provided in the present disclosure.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user (e.g., a physician, a nurse, a healthcare provider, a patient). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for enabling the user to instruct the computer system 1101 to begin sample collection, preparation, processing, loading, separation and/or detection. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1105. The algorithm can, for example, implement the general operation of a system for sample collection, preparation, processing, loading, separation and/or detection.

Samples and Applications

Methods and systems provided herein may be used for diagnosing, detecting, identifying a disease in a subject by (i) detecting or identifying a presence or absence of one or more substances (e.g., biomarkers) in a sample of the subject and/or (ii) measuring or determining a concentration or relative amount of subsets of the molecules and/or compositions in the sample of the subject. Methods and systems of the present disclosure can also be used for monitoring the progression and therapeutic responses of a disease in a subject by (i) detecting or identifying a presence or absence of one or more substances (e.g., biomarkers) in a sample of the subject and/or (ii) measuring or determining a concentration or relative amount of subsets of the substances in the sample of the subject. Methods and systems described herein can further be used for detecting or determining certain risks associated with a disease in a subject by (i) detecting or identifying a presence or absence of one or more substances (e.g., biomarkers) in a sample of the subject and/or (ii) measuring or determining a concentration or relative amount of subsets of the substances in the sample of the subject.

Any substance that is measurable may be the source of a sample. The substance may be a fluid, e.g., a biological fluid. A fluidic substance may include, but not limited to, blood (e.g., whole blood, plasma), cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof.

The substance may be solid, for example, a biological tissue. The substance may comprise normal healthy tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

The substance may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The tumors may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

The substances may comprise a mix of normal healthy tissues or tumor tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

In some cases, the substance may comprise a variety of cells, including, but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, and circulating cells in the human blood. In some cases, the substance may comprise contents of a cell, such as, for example, the contents of a single cell or the contents of multiple cells.

In some cases, the substances may comprise one or more markers whose presence or absence is indicative of some phenomenon such as disease, disorder, infection, or environmental exposure. A marker can be, for example, a cell, a small molecule, a macromolecule, a protein, a glycoprotein, a carbohydrate, a sugar, a polypeptide, a nucleic acid (e.g., deoxyribonucleic acid (DNA), ribonucleic acid (RNA)), a cell-free nucleic acid (e.g., cf-DNA, cf-RNA), a lipid, a cellular component, or combinations thereof.

In some cases, a marker can be a biomarker. Non-limiting examples of biomarkers may include glycated proteins, glycated hemoglobin (HbA1c), HbA-Glyc, HbA-SNO, glycated albumin (GA), glucose (e.g., fasting plasma glucose), human serum albumin (HSA), HSA-Cys, HSA-Glyc, apolipoprotein A-I (apoA-I), apoA-I MetO, GA, glycated apolipoprotein A-1 (GapoA-I), Alpha-fetoprotein (AFP), philadelphia chromosome (BCR-ABL), breast cancer type 1 susceptibility protein (BRCA1), breast cancer type 2 susceptibility protein (BRCA2), v-Raf murine sarcoma viral oncogene homolog B (BRAF V600E), carcinoma antigen 125 (CA-125), carbohydrate antigen 19-9 (CA19.9), Zn-α2 glycoprotein (ZAG), carcinoembryonic antigen (CEA), epidermal growth factor receptor (EGFR), receptor tyrosine-protein kinase erbB-2 (HER-2), mast/stem cell growth factor receptor (KIT), prostate-specific antigen (PSA), S-100 proteins (S100), total tau (T-tau), hyperphosphorylated tau (P-tau), 42 amino acid isoform of amyloid β (Aβ42), cytokines (e.g., interleukin (IL)-1, IL-6, IL-8, Il-10, IL-1β, IL-1Ra, TNF-α monocyte chemoattractant protein-1 (MCP-1) etc.), soluble CD40 ligand, serum amyloid A (SAA), selectins (e.g., E-selectin, P-selectin), myeloperoxidase (MPO), matrix metalloproteinases (MMPs), cellular adhesion molecules (e.g., intercellular adhesion molecule 1 (ICAM-1), vascular adhesion molecule 1 (VCAM-1)), placental growth factor (PlGF), $A_2$ phospholipases, high-sensitivity C-reactive protein (hs-CRP), metalloproteinases (MMP-9, MMP-11), pregnancy-associated plasma protein A (PAPP-A), cathepsin S, chemotactic molecules (MCP-1, CCR1, CCR2), myeloperoxidase, neopterin, growth differentiation factor-15, placental growth factor, markers of fibrosis (e.g., galectin-3), fetuin-A, vascular calcification (osteoprogenterin), myeloid-related proteins 8/14 (MRP8/14), pentraxin 3 (PTX3), osteoprotegerin, von Willebrand factor (vWF), tissue factor (TF), soluble CD40 ligand (sCD40L), prothrombin fragment 1.2 (F1.2), thrombus precursor protein (TpP), D dimer, Lp-PLA2 mass, oxidized amino acids, oxidised apolipoprotein A1 (apoA1), asymmetric dimethylarginine (ADMA), secretory phospholipase, high-sensitivity cardiac troponin, malondialdehyde-modified low-density lipoprotein, heart-type Fatty Acid-Binding Protein (H-FABP), B-type natriuretic peptide (BNP), N-terminal pro b-type natriuretic peptide (NT-proBNP), copeptin, mid-region pro-adrenomedullin, urocortin-1, arginine vasopressin (AVP), endothelin-1, galectin-3, ST-2, cystatin-C, neutrophil gelatinase-associated lipocalin (NGAL), KIM, adiponectin, leptin, resistin, c-peptide, phospholipid fatty acids (EPA and DHA), apolipoprotein E (ApoE), Cholesteryl ester transfer protein (CETP), S100 calcium binding protein B (S100 Beta), Neuron-specific enolase (NSE), and fractions, derivatives or combinations thereof.

Samples may be obtained from various subjects at various time intervals. In some examples, samples are obtained from a subject at least every 30 seconds, 1 minute, 10 minutes, 30 minutes, 1 hour, 2 hours, 3 hours, 4 hours, 5 hours, 6 hours, 12 hours, 1 day, 1 month, or longer.

A sample may be obtained from a subject using various approaches. For example, a sample may be obtained from a subject through accessing the circulatory system (e.g., intravenously or intra-arterially via a syringe, fingerstick, fingerprick, or other apparatus), collecting a secreted biological sample (e.g., saliva, sputum urine, feces, etc.), surgically (e.g., biopsy) acquiring a biological sample (e.g., intraoperative samples, post-surgical samples, etc.), swabbing (e.g., buccal swab, oropharyngeal swab), or pipetting. Such approaches may be used to obtain a biological sample of substantially low volume (e.g., less than or equal to about 5 microliters) form the subject.

Sample can be transported to a facility for analysis. The facility may be onsite or a local facility, e.g., a facility within a clinic or hospital where the sample is collected. The facility may also be an offsite or remote facility which may necessitate shipment of samples.

Samples may be stored and transported in a container. The container may be the same as the sample collection container. The container may be a transport container. The transport container may contain the sample collection container. The transport container may comprise one or more of indentations configured to accommodate one or more of sample containers. The transport container may be in communication with the sample collection container. The transport container may be empty. The transport container may comprise a secondary container. The transport container may be insulated. The secondary container may be insulated. The secondary container may be hermetically sealed. The transport container may comprise a plurality of cooling packets containing a cryogenic material (e.g., cooling packs or dry ice). The transport container may comprise a desiccant. Non-limiting examples of desiccants may include silica, activated charcoal, calcium sulfate, calcium chloride, molecular sieves, or combinations thereof. The desiccant may have a dye indicator. The dye indicator can be reactive with moisture. The transport container may comprise a temperature control module to maintain a pre-set shipping temperature. The transport container can be accommodated in an incubator. The transport container can be heated in an incubator. The transport container may be part of, or integrate with, a system for keeping cells alive. The transport container can comprise a data-logging device. The data-logging device can be programmable. The data-logging device may be configured to monitor and record the change of one or more of parameters concerning the sample during transportation. Non-limiting examples of parameters may include temperature, moisture, pressure, gas level, or a combination thereof. The data-logging device may generate a report regarding the status of the sample being shipped. The data-logging device may directly contact the transport container. The data-logging device may be attached to the transport container. The data-logging device may be separable with the transport container.

The shipping or handling time for each sample may vary depending upon, e.g., the method by which the sample is collected or prepared. The total shipping and handling time as measured from sample collection until sample processing may be less than 1 hour, less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 13 hours, less than 14 hours, less than 15 hours, less than 16 hours, less than 17 hours, less than 18 hours, less than 19 hours, less than 20 hours, less than 21 hours, less than 22 hours, less than 23 hours, or less than 24 hours. In some cases, a shipped sample may be time-stamped to provide a measure of shipping and handling times.

A sample may or may not be processed before being delivered into the microfluidic device for detection and analysis. In cases where a sample processing is needed, various types of processing methods or techniques may be employed. An exemplary processing method may include, for example, (i) diluting an aliquot of each sample with a certain amount of buffer (e.g., phosphate buffered saline (PBS)) and centrifuging the mixture (or diluted sample) under certain conditions (e.g., at a speed of 3,000 g for 5 min at room temperature (RT)); (ii) reconstituting an aliquot (e.g., 5 µL) of the supernatant in a solvent, and subsequently centrifuging the mixture under certain conditions (e.g., at 14,000 g for 5 min at RT) to remove any cellular debris; (iii) collecting the supernatant obtained from step (ii) and storing it as the plasma portion; (iv) washing the cell pellet derived from the first centrifuge step with a buffer (e.g., PBS buffer) at least one time and incubating the washed pellet under certain conditions (e.g., for 2 hours at 37° C.); (v) lysing the cells by, e.g., suspending the cell pellet in certain amount of HPLC-grade water and vortexing for a period of time at RT, constituting the hemolysate in the solvent and centrifuging, e.g., at 14,000 g for 5 min. A certain amount of supernatant may then be collected and stored as the hemolysate portion. Finally, an artificial mixture of a solution may be generated by mixing at least a part of the plasma portion, the hemolysate portion and the solvent. An aliquot of the artificial mixture may then be injected onto the microfluidic device for analysis.

A quantity of total input sample that can be used in the methods provided herein may vary. In some cases, a high quantity of input sample may be used. In some cases, a low quantity of input sample may be used. In some cases, the quantity of input samples may be greater than or equal to about 1 picogram (pg), 10 pg, 25 pg, 50 pg, 100 pg, 250 pg, 500 pg, 750 pg, 1 nanogram (ng), 5 ng, 10 ng, 25 ng, 50 ng, 75 ng, 80 ng, 90 ng, 100 ng, 200 ng, 300 ng, 400 ng, 500 ng, 600 ng, 700 ng, 800 ng, 900 ng, 1 microgram (µg), 2 µg, 3 µg, 4 µg, 5 µg, 6 µg, 7 µg, 8 µg, 9 µg, 10 µg, 12 µg, 14 µg, 16 µg, 18 µg, 20 µg, 25 µg, 30 µg, 35 µg, 40 µg, 50 µg, 40 µg, 70 µg, 80 µg, 90 µg, 100 µg, 200 µg, 300 µg, 400 µg, 500 µg, 750 µg, 1 milligram (mg), 5 mg, 10 mg, 25 mg, 50 mg, 75 mg, 100 mg or more. In some cases, the quantity of input samples may be less than or equal to about 1 gram (g), 500 mg, 250 mg, 100 mg, 50 mg, 25 mg, 10 mg, 5 mg, 1 mg, 750 µg, 500 µg, 250 µg, 125 µg, 100 µg, 75 µg, 50 µg, 40 µg, 30 µg, 25 µg, 20 µg, 19 µg, 18 µg, 17 µg, 16 µg, 15 µg, 14 µg, 13 µg, 12 µg, 11 µg, 10 µg, 9 µg, 8 µg, 7 µg, 6 µg, 5 µg, 4 µg, 3 µg, 2 µg, 1 µg, 900 ng, 800 ng, 700 ng, 600 ng, 500 ng, 400 ng, 300 ng, 200 ng, 100 ng, 75 ng, 50 ng, 25 ng, 10 ng, 5 ng, 1 ng, 750 pg, 500 pg, 250 pg, 100 pg, 50 pg, 25 pg, 10 pg, 1 pg or less. In some cases, the quantity of input sample may fall into a range between any two of the values described herein.

In some examples, input sample may comprise one or more substances that are to be detected or identified. The substances of interest or the target substances (e.g., substances associated with a disease or disorder) may make up a certain percentage of the total sample input. For example, a sample may comprise a plurality of proteins and only a few of the proteins (e.g., 5% or less, 1% or less) that are associated with or indicative of certain type of diseases or conditions are the substances of interest. In some cases, the target substances may make up a high percentage of the total input. In some cases, the target substances may make up a low percentage of the total input. In some cases, the target substances may make up less than or equal to about 100%, 95%, 90%, 80%, 70%, 60%, 50%, 40%, 30%, 20%, 10%, 5%, 1%, 0.75%, 0.5%, 0.25%, 0.1%, 0.075%, 0.05%, 0.025%, 0.01%, 0.0075%, 0.005%, 0.0025%, 0.001%, 0.00075%, 0.005%, 0.0025%, 0.001%, 0.00075%, 0.0005%, 0.00025%, 0.0001%, 0.000075%, 0.00005%, 0.000025%, 0.00001% or less of the total input. In some cases, the target substances may make up at least about 0.000001%, 0.000005%, 0.0000075%, 0.00001%, 0.00005%, 0.000075%, 0.0001%, 0.0005%, 0.00075%, 0.001%, 0.005%, 0.0075%, 0.01%, 0.05%, 0.075%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, 99%, 99.99% or more of the total input. In some cases, the percentage of the target substances may be between any of the two values described herein.

The quantity of input target substances may vary. In some cases, a high quantity of target substances may be included. In some cases, a low quantity of target substances may be included. In some cases, at least about 1 femtogram (fg), 5 fg, 10 fg, 25 fg, 50 fg, 100 fg, 200 fg, 300 fg, 400 fg, 500 fg, 600 fg, 700 fg, 800 fg, 900 fg, 1 pg, 5 pg, 10 pg, 25 pg, 50 pg, 100 pg, 200 pg, 300 pg, 400 pg, 500 pg, 600 pg, 700 pg, 800 pg, 900 pg, 1 ng, 2.5 ng, 5 ng, 10 ng, 25 ng, 50 ng, 75 ng, 100 ng, 200 ng, 300 ng, 400 ng, 500 ng, 600 ng, 700 ng, 800 ng, 900 ng, 1 µg, 2 µg, 3 µg, 4 µg, 5 µg, 6 µg, 7 µg, 8 µg, 9 µg, 10 µg, 15 µg, 20 µg, 30 µg, 40 µg, 50 µg, 75 µg, 100 µg, 250 µg, 500 µg, 750 µg, 1 mg, 10 mg, 25 mg, 50 mg, 100 mg or more of target substances may be inputted. In some cases, less than or equal to about 1 g, 500 mg, 250 mg, 100 mg, 50 mg, 25 mg, 10 mg, 5 mg, 1 mg, 750 µg, 500 µg, 250 µg, 100 µg, 80 µg, 60 µg, 50 µg, 40 µg, 30 µg, 20 µg, 18 µg, 16 µg, 14 µg, 12 µg, 10 µg, 9 µg, 8 µg, 7 µg, 6 µg, 5 µg, 4 µg, 3 µg, 2 µg, 1 µg, 900 ng, 800 ng, 700 ng, 600 ng, 500 ng, 400 ng, 300 ng, 200 ng, 100 ng, 75 ng, 50 ng, 25 ng, 10 ng, 5 ng, 1 ng, 500 pg, 250 pg, 100 pg, 50 pg, 25 pg, 10 pg, 5 pg, 1 pg or less of target substances may be inputted. In some cases, the quantity of inputted target substances may fall into a range between any of the two values described herein.

A volume of the sample that can be used in the methods provided herein may vary. As provided herein, methods and systems can be adapted or configured to perform functions on a sample having either a large or a small volume. As will be appreciated, in some cases, it may be preferred to have methods or systems that can support highly-sensitive analysis on very little sample.

For example, in some cases, less than or equal to about 1000 µL, 900 µL, 800 µL, 700 µL, 600 µL, 500 µL, 400 µL, 300 µL, 200 µL, 100 µL, 90 µL, 80 µL, 70 µL, 60 µL, 50 µL, 45 µL, 40 µL, 35 µL, 30 µL, 25 µL, 20 µL, 15 µL, 10 µL, 9 µL, 8 µL, 7 µL, 6 µL, 5 µL, 4 µL, 3 µL, 2 µL, 1 µL, 900 nL, 800 nL, 700 nL, 600 nL, 500 nL, 400 nL, 300 nL, 200 nL, 100 nL, 75 nL, 50 nL, 25 nL, 10 nL, 1 nL, 750 picoliter (pL), 500 pL, 250 pL, 100 pL, 75 pL, 50 pL, 25 pL, 10 pL, 5 pL, 1 pL or less of the sample may be used. In some cases, the volume of input sample may be between any of the two values described herein.

A variety of diseases, conditions or disorders may be studied, diagnosed and/or monitored by the methods and systems provided in the present disclosure. In some cases, the diseases are diabetes, such as Type-1 Diabetes (T1D), Type-2 Diabetes (T2D), or Gestational Diabetes Mellitus (GDM). However, other disease or conditions may be studied, diagnosed and/or monitored using methods and system provided herein. Disease study, diagnosis and/or monitoring can include detecting one or more biomarkers that are indicative of the disease in a sample from a subject.

For example, methods and systems provided herein may be used to study, diagnose and/or monitor neoplastic conditions, including, but not limited to, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia,Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

Cardiovascular diseases may be studied, diagnosed and/or monitored by methods and systems provided herein. Examples of cardiovascular disease include, but are not limited to, coronary heart disease, ischemic heart disease, cardiomyopathy, hypertensive heart disease, pulmonary heart disease, congestive heart failure, inflammatory heart disease, valvular heart disease, cerebrovascular disease, peripheral arterial disease, congenital heart disease, rheumatic heart disease, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic night ventricular dysplasia, hypertrophic cardiomyopathy, Williams syndrome, heart valve diseases, endocarditis, bacterial, pulmonary atresia, aortic valve stenosis, Raynaud's disease, Raynaud's disease, cholesterol embolism, Wallenberg syndrome, Hippel-Lindau disease, and telangiectasis.

Autoimmune disorders may be studied, diagnosed and/or monitored by the methods and systems provided herein. Examples of autoimmune disorders may include, but not limited to, Crohn's disease, ulcerative colitis, psoriasis, psoriatic arthritis, juvenile arthritis and ankylosing spondilitis, Other non-limiting examples of autoimmune disorders include autoimmune diabetes such as T1D, multiple sclerosis, systemic lupus erythematosus (SLE), rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome. Undesirable immune response can also be associated with or result in, e.g., asthma, emphysema, bronchitis, psoriasis, allergy, anaphylaxsis, auto-immune diseases, rhuematoid arthritis, graft versus host disease, transplantation rejection, lung injuries, and lupus erythematosus.

The disease or condition may be an inflammatory condition. The inflammatory condition may be an acute systemic inflammatory disease or a chronic inflammatory disease. Examples of inflammatory conditions may include but not limited to systemic inflammatory response syndrome (SIRS), ARDS, sepsis, inflammatory bowel disease, inflammatory skin diseases, psoriasis, eczema, scleroderma severe sepsis, septic shock erysipelas, meningitis, arthritis, rheumatoid arthritis, toxic shock syndrome, diverticulitis, appendicitis, pancreatitis, cholecystitis, colitis, cellulitis, burn wound infections, pneumonia, urinary tract infections, postoperative infections, peritonitis cystic fibrosis, COPD and other pulmonary diseases, gastrointestinal disease including chronic skin and stomach ulcerations, atopic dermatitis, oral ulcerations, aphtous ulcers, genital ulcerations and inflammatory changes, parodontitis, eye inflammations including conjunctivitis and keratitis, external otitis, mediaotitis and genitourinary inflammations.

Methods and systems provided herein may be utilized for diagnosing and/or monitoring the progression and therapeutic responses of Huntington's Disease, Parkinson's Disease, Alzheimer's disease (AD) or any other neurodegenerative diseases including but not limited to Alexander's disease, Alper's disease, ataxia telangiectasia, Batten disease, bovine spongiform encephalopathy, Canavan disease, Cockayne syndrome, corticobasal degeneration, Creutzfeldt-Jakob disease, HIV-associated dementia, Kennedy's disease, Krabbe's disease, lewy body dementia, Machado-Joseph disease, multiple sclerosis, multiple system atrophy, narcolepsy, neuroborreliosis, Pelizaeus-Merzbacher Disease, peripheral neuropathy, Pick's disease, primary lateral sclerosis, prion diseases, Refsum's disease, Sandhoffs disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes dorsalis.

Methods and systems provided herein may be utilized for diagnosing and/or monitoring the ionizing radiation (IR) damage to the body of a subject and the subsequent diseases arising from the radiation damage. Example biomarkers of acute and delayed radiation injury after a radiological/nuclear terrorist incident may comprise those that arise and are measurable prior to manifestation of tissue injuries, for example, one to a few days after IR exposure. They may be measurable in a non-invasive or minimally invasive way, e.g., using peripheral blood. The microfluidic chips disclosed herein can simultaneously detect cellular and molecular markers associated with IR-induced cellular and molecular changes using peripheral blood. Further, the microfluidic chips disclosed herein can diagnose and monitor the consequential diseases such as cancer as a result of IR.

EXAMPLES

Example 1

Microfluidic Device and its Assembly

The single-plex MEA chips are designed using the L-Edit software (v15, Tanner Research). The design contains a three-layer Si—Si-glass structure that monolithically integrated several functional modules on a single chip. Specifically, the emitters are constructed between the two silicon layers while all the other functional components (including the LC and trap columns) are built between the glass and silicon layers. A through-hole in the middle silicon layer is produced to connect emitters with LC channels. The silicon layers offer the ease for fabricating complex structures while the glass cover provides the imaging window for real-time monitoring of on-chip processes such as the bead packing. MEA chips are examined by light microscopes and scanning electron microscope (SEM) for integrity of each component.

FIGS. 1a and 1b show an example microfluidic device and its assembly. As shown in FIG. 1a, the device contains a Si—Si-glass three-layer structure. An emitter is constructed between two silicon layers. All the other functional components including a trap column and a LC-column are produced between the silicon and glass layers. High-resolution photographs in FIG. 1b show the device and its assembly with a custom-built manifold and fittings, relative to a US quarter. The dimensions of the LC column are 5 cm (length)×100 μm (width)×100 μm (depth) and the trap column is 1 cm (length)×300 μm (width)×120 μm (depth). The microfabricated emitter has nozzles with a cross-section of 25 μm×25 μm and a protruding length of 120 μm.

Example 2

Fabrication Process for the Microfluidic Device

As shown in FIG. 2, fabrication process includes (a) cleaning of 6-inch silicon wafers with a piranha solution; (b) standard photolithography and deep reactive ion etching (DRIE) to create emitters; (c) photolithography and DRIE etching to create columns on the backside of the wafer; (d) standard photolithography and through-wafer DRIE etching to create access holes; (e) thermal fusion after contacting to another clean wafer, and annealing them to form covalent Si—Si fusion bonding; (f) growth of thermal oxide on all surfaces; (g) photolithography and through-wafer DRIE to sharpen the left and right sides of emitters; (h) anodic bonding of the silicon pair with a glass wafer; (i) polishing and sharpening of the top and bottom sides of emitters by the sand paper; and (j) XeF2 etching to protrude the nozzles.

Example 3

Packing and Testing of On-Chip LC Columns

A 3 μm frit is implemented between the LC channel and nozzles to retain beads. LC and enrichment (trap) channels are packed with Magic-C4 5 μm beads (pore size of 300 Å, Bruker-Michrom) by an in-house column packing station. Briefly, beads are suspended in methanol and sonicated to form a solution of mono-dispersed particles. The slurry of particles is then forced into the channels on the chip through the sample input holes by a pressurized (>1000 psi) helium gas tank. The pressure gauge is shut off in 20 minutes and the system is slowly depressurized for about one hour before switching to the atmosphere pressure. Helium gas is purged afterwards to dry out the bead beds. Finally, the backend of the packed channels are sealed by fabricating sol-gel frits to prevent beads from retreating during the LC runs. The sol-gel solution is prepared by mixing 34 μL of Kasil 1 potassium silicate (PQ Corp.) with 6 μL of formamide (Sigma), followed by vortexing and centrifuging for 1 min. A 1 μL aliquot of the sol-gel solution is introduced to a chip reservoir and then flowed into the channel for 2 min. The chip is then incubated on a hot plate at 80° C. for over 6 hours. After the frit is completely polymerized, the columns with sol-gel frits are washed with methanol. The quality and reproducibility of the frit and bead packing are confirmed by microscope examination, followed by backpressure monitoring for the LC channels under a constant flow rate (e.g., 1 μL/min). The efficiency of the LC separation is validated by LC-MS analysis of standard proteins mixtures.

Example 4

Preparation of Standard Samples for Validating MEA Chips

Pure HbA1c and HbA0 (IFCC reference material) are obtained from Lee Biosolutions (St. Louis, Mo.). Lyphochek® hemoglobin A1c linearity set (LOT #34650, level 1-4) is obtained from Bio-Rad (Hercules, Calif.). All other chemicals and biologics are obtained from Sigma-Aldrich (St. Louis, Mo.). For ESI-MS response curve of HbA1c/HbA, calibrator solutions are prepared by mixing pure HbA0 and HbA1c solutions in LC solvent A (5/95 acetonitrile (ACN)/$H_2O$ with 0.2% formic acid (FA)). A set of calibrators with five levels of HbA1c (0, 1.9, 5.7, 10.7 and 16.7%) are prepared in triplicate and each replicate is analyzed at least 3 times. HbA1c linearity set samples are stored at −20° C. Right before use, the samples are thawed and incubated at 37° C. for 10 min, and then diluted 1:1000 in solvent A for LC-MS analysis. For LC-MS response curve of glucose/D-(+) glucose-6,6-d2 (hereafter: glucose-d2), calibrator solutions are prepared by mixing pure glucose and glucose-2d solutions, and subsequently spiked in the pooled plasma that is diluted 1:100 in solvent A. The concentration of glucose-2d in the final solution is fixed at 50 μM. A set of calibrators with five concentrations of glucose (0, 20, 50, 100 and 250 μM) are prepared in triplicate and each replicate is analyzed at least 3 times.

Example 5

Processing of Blood Samples for LC-MS Analysis

A capillary liquid chromatography system (CapLC) (Waters Corp.) is used to deliver nanoflow LC gradient on the MEA chip. A volume of 4 μL of the processed whole blood sample is injected through an autosampler onto the on-chip trap column with a flow rate of 20 μL/min. The on-chip LC column is run at a flow rate of 600 nL/min. The solvent A consists of 5/95 ACN/$H_2O$ with 0.2% FA, and solvent B consists of 95/5 ACN/$H_2O$ with 0.2% FA. The LC gradient starts at 1% B and is held at 1% B for 3 minutes. Starting at 3 min, it is linearly increased to 20% B in 5 minutes, and then ramped up again to 50% in 42 minutes. After that, it is further increased to 95% B in 5 minutes and finally returned to the initial condition (1% B) in another 5 minutes. MS detection is performed on a hybrid quadrupole/orthogonal Q-TOF API US mass spectrometer (Waters Corp.) The capillary voltage is set to be 3.2 kV and cone voltage is 40

V. Nanoelectrospray process on MEA emitters is visualized and monitored using a Waters nanoflow camera kit equipped with a MLH-10 Zoom lenses (Computar).

The raw LC-MS data are processed using the MassLynx 4.0 software package provided with the Q-TOF instrument. Extracted ion chromatograms (EIC) for all target proteins are generated using their corresponding ions of the charge state at the maximum intensity. The entire peak region in the EIC for each protein is summed to acquire their integrated mass spectra. The integrated mass spectrum (m/z 750-1350 for HbA and apoA-I, m/z 1100-1400 for HSA) is then deconvoluted onto a mass scale using the maximum entropy-based algorithm (MaxEnt 1) in MassLynx 4.0. The parameters for MaxEnt 1 are chosen as the following: mass range 12,000-18,000 Da for HbA, 63,000-69,000 Da for HSA, and 24,000-32,000 Da for apoA-I; resolution 0.1-0.2 Da/channel. The uniform Gaussian peak width at the half-height for each protein is determined using its highest intensity peak. The left and right minimum intensity ratio is set to be 40% for HbA, 85% for HSA, and 80% for apoA-I. Finally, the MaxEnt 1 deconvoluted spectrum is baseline-subtracted with a 25-order polynomial, smoothed (2×6 Da Savitzky-Golay), and centered (centroid top 80%) with areas created. The ion intensities in the centered spectra, which employed the corresponding peak areas, are used to quantify each protein isoform. For HbA1c, the response curve is generated using the pure protein standards. For HSA and apoA-I isoforms, similar MS responses for unmodified proteins and their different adducts (e.g., HSA-Cys and HSA-Glyc) are assumed. Following are the details for calculating the relative level of each protein isoform.

Figure 6A:
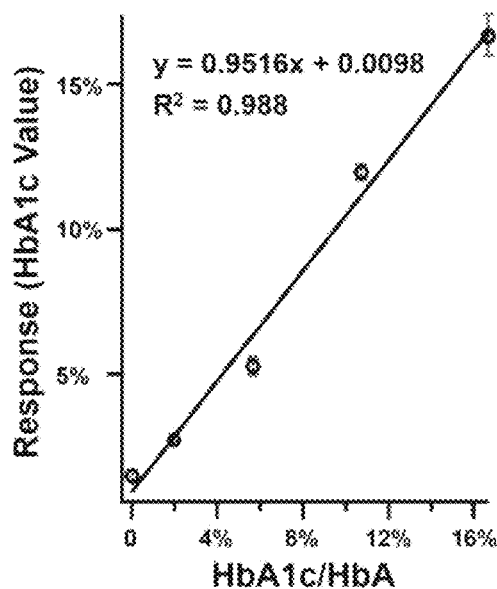
FIGS. 6a-6d show the validation of an example top-down-proteomics-centric assay for diabetes monitoring.

HbA1c value is calculated using the ratio between the peak area (I) of the charge deconvoluted peak of HbA-β-Glyc (mass, 16029 Da) and those of all prominent HbA-β isoforms including HbA-β (mass, 15867 Da), HbA-β-SNO (mass, 15897 Da), and HbA-β-Glyc, and normalized by the ESI-MS response factor determined from the slope of the response curve in FIG. 6a. The equation is:

$$HbA1c = I(HbA\text{-}\beta\text{-}Glyc)/((I(HbA\text{-}\beta) + I(HbA\text{-}\beta\text{-}SNO) + I(HbA\text{-}\beta\text{-}Glyc)) \times 0.9516),$$

where I represents the peak area of the charge-deconvoluted peaks, and 0.9516 is the response factor.

Similarly, the relative level of HbA-SNO is calculated as:

$$HbA\text{-}SNO = I(HbA\text{-}\beta\text{-}SNO)/(I(HbA\text{-}\beta) + I(HbA\text{-}\beta\text{-}SNO) + I(HbA\text{-}\beta\text{-}Glyc))$$

The relative level of glycated albumin (GA) is calculated as:

$$GA = (I(HSA + 1Glyc) + I(HSA\text{-}Cys + 1Glyc) +$$
$$2 \times I(HSA + 2Glyc) + 2 \times I(HSA\text{-}Cys + 2Glyc))/$$
$$(I(HSA) + I(HSA\text{-}Cys) + I(HSA + 1Glyc) + I(HSA\text{-}Cys + 1Glyc) +$$
$$I(HSA + 2Glyc) + I(HSA\text{-}Cys + 2Glyc))$$

Double weighting of the doubly glycated form of HSA are used to account for two glycations per HSA. The denominator contains all identifiable HSA peaks and represented the total HSA.

The relative level of HSA-Cys is calculated as:

$$HSA\text{-}Cys = (I(HSA\text{-}Cys) + (HSA\text{-}Cys + 1Glyc) + I(HSA\text{-}Cys + 2Glyc))/$$
$$(I(HSA) + I(HSA\text{-}Cys) + I(HSA + 1Glyc) +$$
$$I(HSA\text{-}Cys + 1Glyc) + I(HSA + 2Glyc) + I(HSA\text{-}Cys + 2Glyc))$$

The relative level of apoA-I glycation (GapoA-I) is calculated as:

$$GapoA\text{-}I = (I(apoA\text{-}I + 1Glyc) + I(apoA\text{-}I + 1Glyc + 1MetO) +$$
$$I(apoA\text{-}I + 1Glyc + 2Meto) + I(apoA\text{-}I + 1Glyc + 3MetO))/$$
$$(I(apoA\text{-}I\text{-}Gln) + I(apoA\text{-}I\text{-}Gln + 1MetO) + I(apoA\text{-}I\text{-}Gln + 2MetO) +$$
$$I(apo\text{-}A\text{-}I\text{-}Gln + 3MetO) + I(apoA\text{-}I) + I(apoA\text{-}I + 1MetO) +$$
$$I(apoA\text{-}I + 2MetO) + I(apoA\text{-}I + 3MetO) +$$
$$I(apoA\text{-}I + 1Glyc) + I(apoA\text{-}I + 1Glyc + 1MetO) +$$
$$I(apoA\text{-}I + 1Glyc + 2MetO) + I(apoA\text{-}I + 1Glyc + 33MetO))$$

The denominator contains all identifiable apoA-I peaks and represented the total apoA-I.

The relative level of methionine oxidation of apoA-I (apoA-I MetO) is calculated as the percentage of maximum methionine oxidation capacity of apoA-I, in which all apoA-I molecules are modified by 3 methionine sulfoxides. The intensity of unoxidized, singly, doubly, and triply oxidized apoA-I are multiplied by 0, 1/3, 2/3, and 1, respectively, and then summed to obtain the weighted intensity of the oxidized apoA-I. MetO of all apoA-I isoforms are considered. Hence, apoA-I MetO is obtained by normalizing the weighted intensity of oxidized apoA-I with that of the total apoA-I as:

$$apoA\text{-}I \ MetO =$$
$$\left(I(apoA\text{-}I\text{-}Gln + MetO) \times \frac{1}{3} + I(apoA\text{-}I\text{-}Gln + 2MetO) \times \frac{2}{3} +\right.$$
$$I(apoA\text{-}I\text{-}Gln + 3MetO) + I(apoA\text{-}I + MetO) \times \frac{1}{3} +$$
$$I(apoA\text{-}I + 2MetO) \times \frac{2}{3} + I(apoA\text{-}I + 3MetO) +$$
$$I(apoA\text{-}I + 1Glyc + 1MetO) \times \frac{1}{3} +$$
$$\left.I(apoA\text{-}I + 1Glyc + 2MetO) \times \frac{2}{3} + I(apoA\text{-}I + 1Glyc + 3MetO)\right)/$$
$$(I(apoA\text{-}I\text{-}Gln) + I(apoA\text{-}I\text{-}Gln + 1MetO) + I(apoA\text{-}I\text{-}Gln + 2MetO) +$$
$$I(apoA\text{-}I\text{-}Gln + 3MetO) + I(apoA\text{-}I) + I(apoA\text{-}I + 1MetO) +$$
$$I(apoA\text{-}I + 2MetO) + I(apoA\text{-}I + 3MetO) +$$
$$I(apoA\text{-}I + 1Glyc) + I(apoA\text{-}I + 1Glyc + 1MetO) +$$
$$I(apoA\text{-}I + 1Glyc + 2MetO) + I(apoA\text{-}I + 1Glyc + 3MetO))$$

For statistical analysis, GraphPad Prism 6 software is utilized. For error bars at each data point, at least triplicate experiments (n≥3) are performed to obtain the standard deviation. A Bland-Altman plot is used for the comparison between a sample assay using a MEA chip provided in the present disclosure and the commercial HbA1c assay using a Tosoh G7 instrument. Student's t-test is performed to examine the differences in HbA1c, GA, GapoA-I, HSA-Cys, HbA-SNO, and apoA-I MetO, respectively, between the healthy controls and T2D patients. The p values of t-test are determined by using the unpaired and two-tailed parametric tests without assuming equal variance in both groups. Pearson's correlation is performed to investigate the following relationships: (1) between any two of HbA1c, GA, and GapoA-I; (2) between HSA-Cys and HbA1c, GA, and GapoA-I, respectively; and (3) between age and HSA-Cys, HbA-SNO, and apoA-I MetO, respectively. Pearson's coefficient (r) and p value (two-tailed) are calculated.

Example 6

Monitoring Diabetes Using the Device

Diabetes has become a global epidemic and its patient population may increase drastically in the coming years, according to the International Diabetes Federation. Despite its clinical diagnosis using fasting plasma glucose (FPG) and glycated hemoglobin A (HbA1c) assays and home monitoring using blood glucose meters, one of the major challenges in diabetes management is the longitudinal monitoring of its progression and therapeutic responses.

The most common markers for monitoring patients with diabetes are glucose and HbA1c, but additional markers such as glycated human serum albumin (HSA) identified may address the glycation gap and bridge the timescales of glycemia between transient and 2~3 months. However, there is currently no technical platform that can measure these markers concurrently in a cost-effective manner.

Glucose meters measure the transient blood glucose levels in the plasma, while HbA1c assays measure the average level of HbA glycation inside the red blood cells for the preceding 2-3 months. The glycation gap, defined as the difference between the measured HbA1c and the HbA1c value predicted from glycated serum proteins, has been associated with microvascular complications of diabetes. Therefore, ongoing efforts may incorporate glycated albumin (GA) in the plasma as an additional clinical marker for the average blood glucose level over a period of 2-3 weeks.

A variety of platforms and sample preparation protocols may be utilized to measure glucose, HbA1c, and GA, separately, each using different methods based on liquid chromatography, immunoassay, electrochemistry, and electrophoresis etc. However, it is so far not a routine practice to perform parallel analysis of these markers under the same clinical settings and integrate the results in a timely manner. A unified platform that can concurrently measure multiple classes of diabetes markers including, but not limited to, glucose, HbA1c, and GA, and encompass multiple timescales (e.g., transient, days, weeks, months) of glycemia in a subject will make major contributions to diabetes theranostics and management.

The proteome may reflect a subject's actual physiopathological states at a given time; therefore proteomics may be a powerful tool for diagnostics of diseases and monitoring of their progression and therapeutic responses. The majority of current clinical protein assays rely on the enzyme-linked immunosorbent assay (ELISA), which has several significant limitations: (a) multiplexing greater than approximately 10 antibodies is difficult due to the cross-reactivity of antibodies; (b) antibodies are not available for the vast majority of proteins, particularly for their modified isoforms; and (c) assay development is lengthy and expensive. In contrast, mass spectrometry (MS) may allow multivariate analysis of complex patterns of a plurality of biomarkers without knowing their identities or having specific antibodies available.

The clinical proteomics may be conducted by analyzing low-abundance proteins using either bottom-up proteomics (i.e., analysis of proteolytic peptides) or top-down proteomics (i.e., large-scale identification and characterization of full-length proteins). Since Mass spectrometry allows multivariate analysis of a plurality of analytes, MS-based platform may find useful in clinical diagnostics.

(1) Top-Down-Proteomics-Centric Analysis of Small Volumes of Blood Samples

Figure 3:
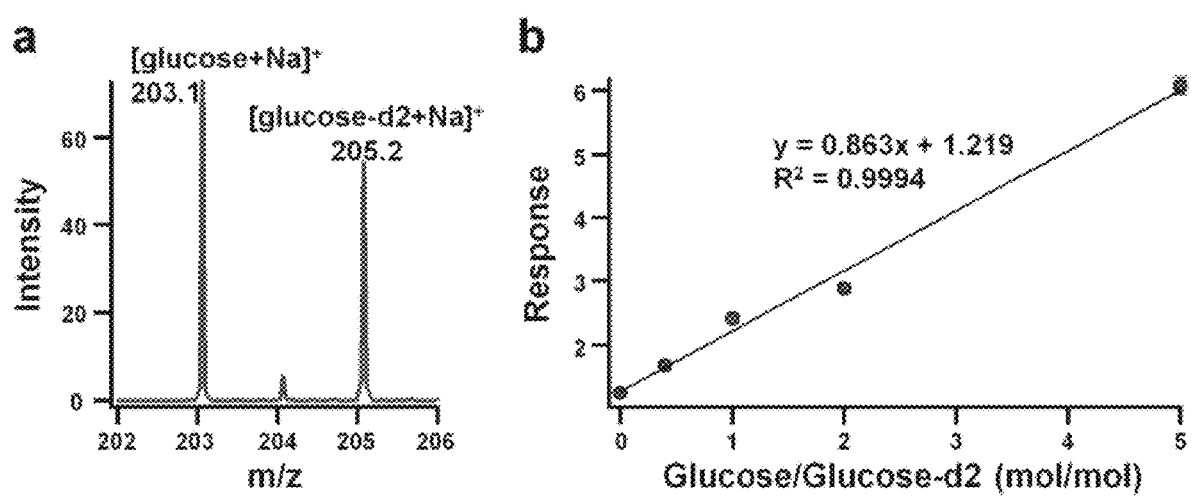
FIG. 3 in panels (a)-(b) shows the quantitation of free glucose in blood samples using the microfluidic device. Panel (a) shows an example LC-nano ESI-MS spectrum of a mixture of standard glucose and glucose-d2. Panel (b) shows an example calibration curve for varying amounts of glucose spiked in the pooled plasma matrix (1:100 dilutions with 1× PBS buffer), with constant 50 µM glucose-d2 spiked in as the internal standards.
Figure 4:
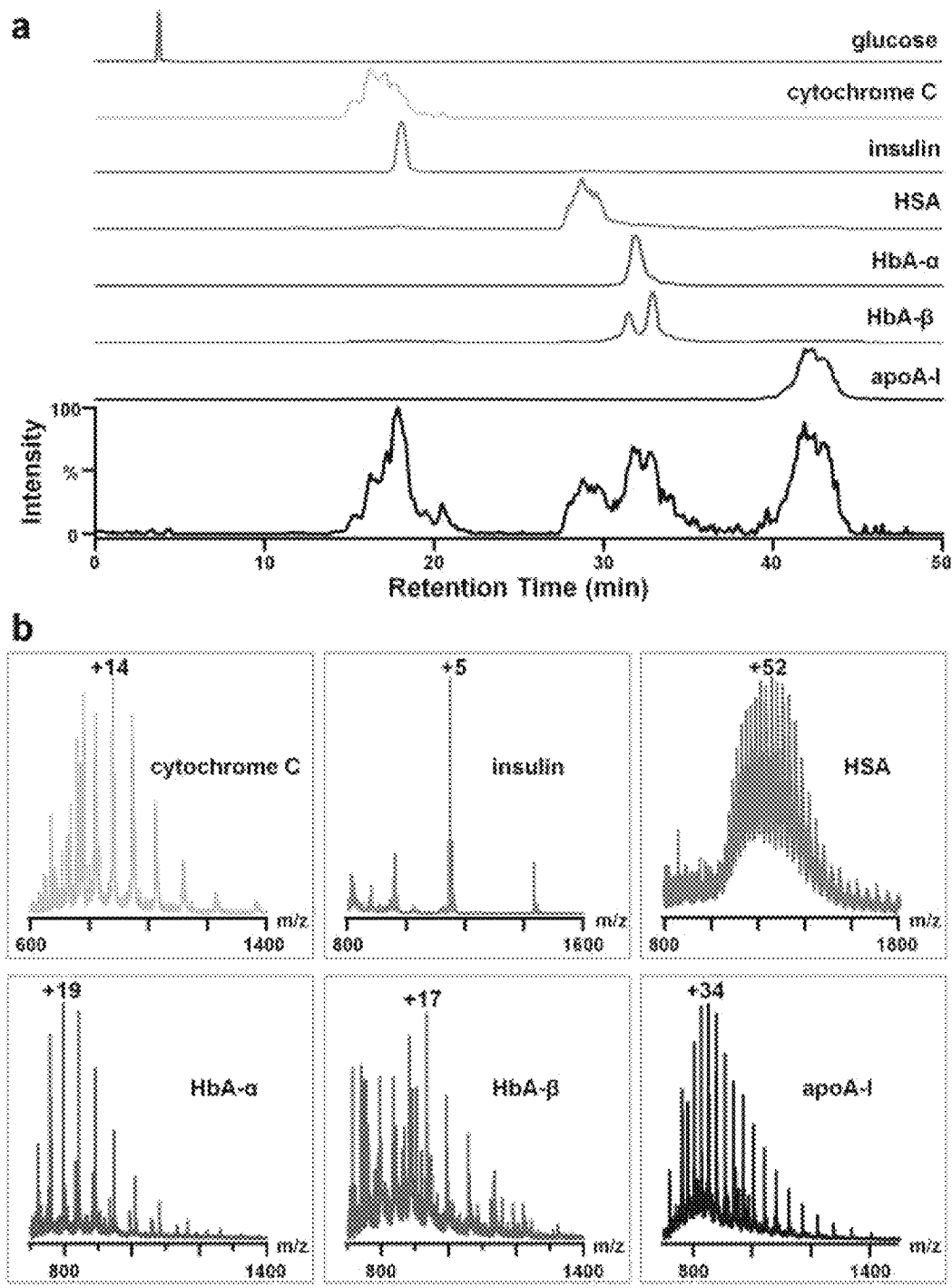
FIG. 4 in panels (a)-(b) shows example LC-MS spectra of glucose and standard proteins analyzed using the microfluidic device. Panel (a) shows an example total ion chromatogram (TIC) for a mixture of glucose and five standard proteins in a one-hour LC-MS run. Panel (b) shows an example ESI-MS spectra of the five proteins, each labeled with their charge state (+N) at the maximum intensity, respectively.
Figure 5:
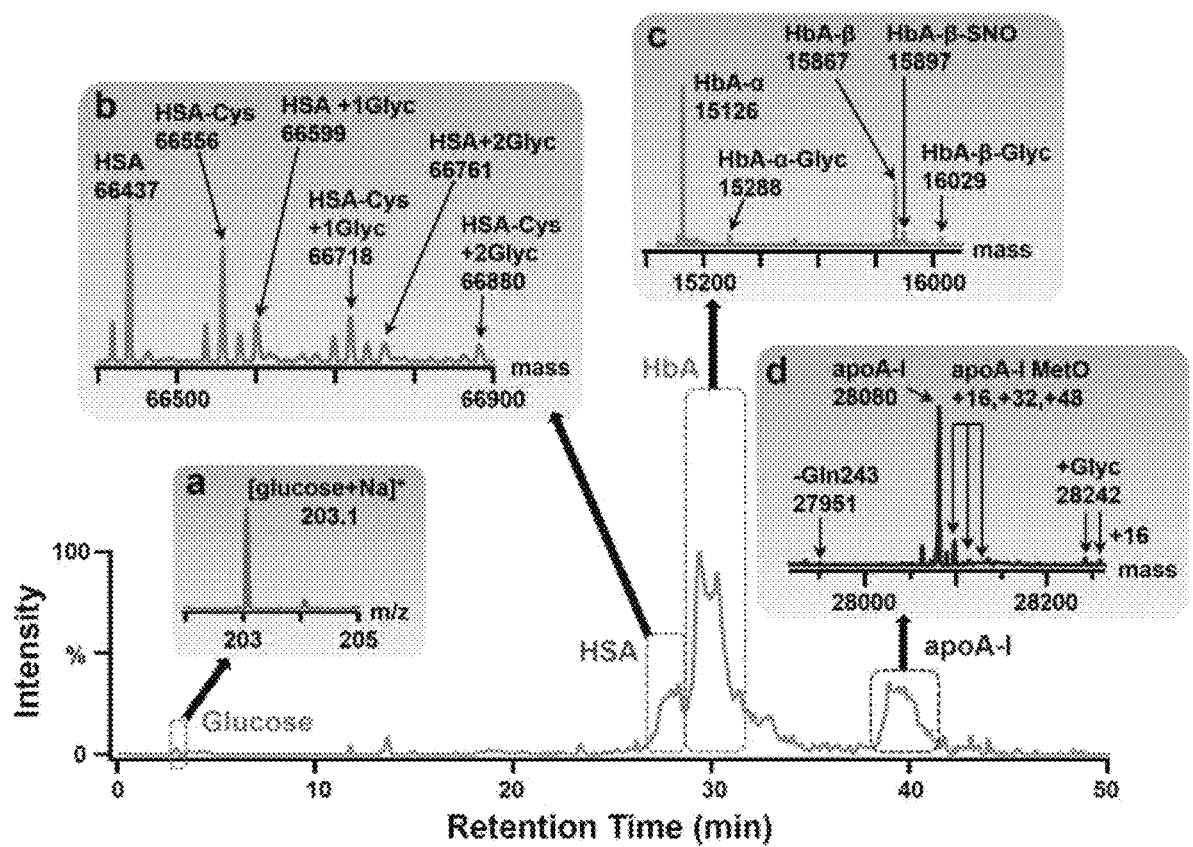
FIGS. 5A-5D show the development of an example top-down-proteomics-centric assay for diabetes monitoring.

FIG. 1b shows an assembly of an example one-plex MEA chip (chip is shown in the insert). Qualitative and quantitative LC-MS analysis of free glucose and abundant blood proteins relevant to hyperglycemia in diabetes including hemoglobin A (HbA), human serum albumin (HSA), and apolipoprotein A-I (apoA-I) are demonstrated (FIG. 4). Extracted ion chromatograms (EIC) for each component including glucose, bovine cytochrome C, bovine insulin, human HSA, human HbA-α and HBA-β, and human apoA-I are shown in the order of their ascending LC elution time, respectively. Using glucose-d2 as the internal standard, the assembly can be used to accurately determine the the free glucose concentrations in the blood using the ratio between the LC-MS peak areas of the Na+ adducts of glucose and glucose-d2 (m/z: 203 and 205, respectively) (FIG. 3). Responses (glucose: glucose-2d) are determined by calculating the ratio between the LC-MS peak areas of glucose and glucose-2d, relative to the given molar ratio of spiked glucose and glucose-2d. The endogenous glucose in the pooled plasma matrix is subtracted in the final calculation. The error bars are too small to be seen (s.d., n≥3). Since glucose has a low hydrophobicity, it is eluted very early in the current one-hour LC gradient on the C4 column that is optimized for LC-MS analysis of proteins. However, the response curve can still be obtained to quantify glucose from LC-MS chromatographs. Since glucose degrades quickly in the whole blood and needs to be measured immediately after the blood draw, the glucose level in whole blood samples may not be quantified. In cases where the glucose level is needed, it can be analyzed in a separate column packed with HILIC (e.g., $NH_2$) beads on a multiplexed MEA chip (e.g., 24-plexed). Quantitation of various isoforms of HSA, HbA, and apoA-I in a pooled plasma sample or a fresh blood sample from a healthy are also performed with the device. LC-MS analysis of standard protein mixtures is first performed to validate the performance of the on-chip C4 column on our MEA chip (FIG. 4). Diluted blood samples corresponding to a mere 0.1 μL of the starting plasma are then analyzed by using the MEA chip. FIG. 5 shows example total ion chromatogram (TIC) for a one-hour LC-MS run of ~0.1 μL whole blood, showing LC-MS peaks for free glucose, HSA, HbA, and apoA-I, respectively. The representative mass spectra of glucose and different isoforms of HSA, HbA, and apoA-I after MaxEnt1 deconvolution are shown in the inserts (a)-(d), respectively. The identified protein modifications include glycation, cysteinylation, nitroslylation, oxidation, and truncation. By comparing the LC-MS chromatographs, MS spectra, charge states, and MaxEnt 1 transformed charge-deconvoluted peaks (inserts) (FIG. 5), various modifications (cysteinylation, glycation, nitroslylation, and methionine oxidation, etc.) of these proteins in the blood are identified. Specifically, for HSA, its multiple species are detected, including unmodified, cysteinylated (at Cys34), glycated (dominantly at Lys1125), both cysteinylated and glycated, and doubly glycated isoforms; for HbA, glycation at both α and β chains, and nitroslylation at β chain (at Cys93) are identified; for apoA-I, glycation (hereafter: GapoA-I), and oxidation at 1-3 methionine residues (hereafter: apoA-I MetO) etc. are identified. Protein nitrosylation and cysteinylation at Cysteine residues are important for signal transduction in response to oxidative stress, while glycation of HbA (and HSA) is an example marker for glucose metabolism and can be used for diabetes diagnosis.

(2) Diabetes Monitoring

Figure 6B:
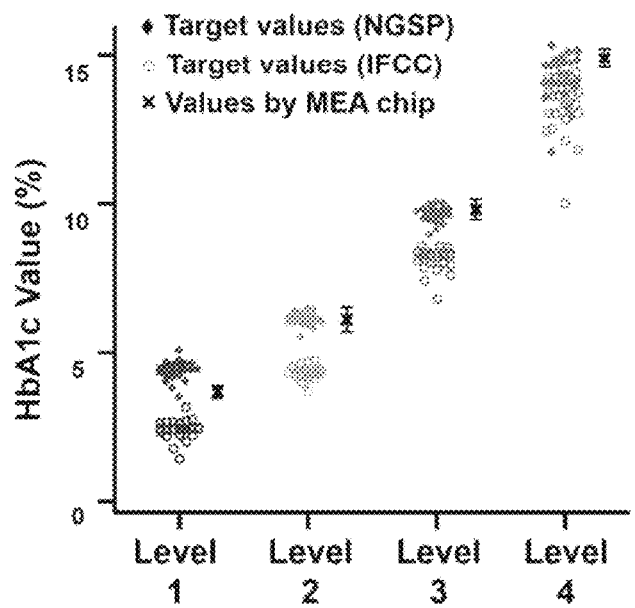
Figure 6C:
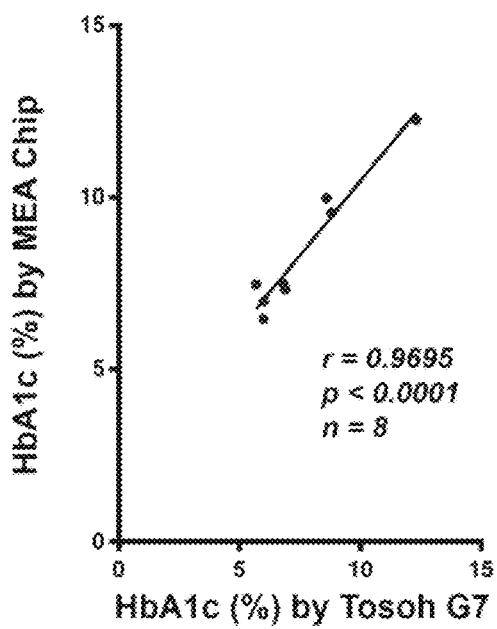
Figure 6D:
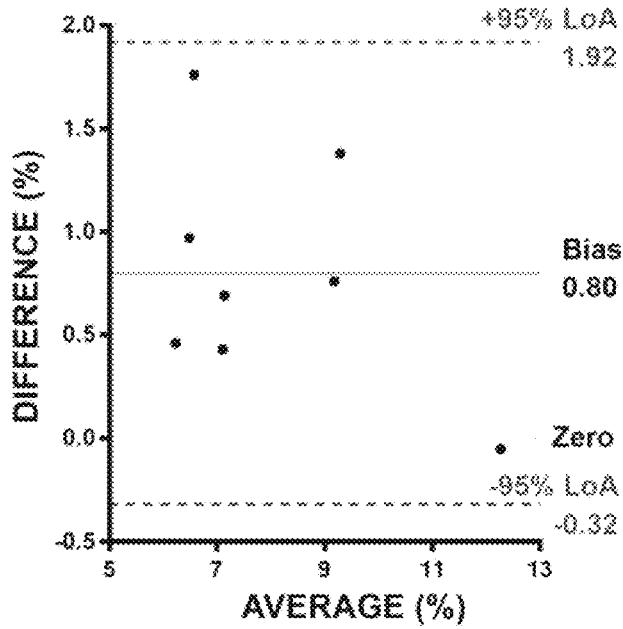

As shown in FIG. 6a, a LC-MS calibration curve with a response factor of 0.9516 for the HbA1c/HbA ratio is obtained by using HbA1c (HbA glycated at the N-terminus of β chain) as the example. Based on this response curve, the HbA1c values for the Bio-Rad Lyphochek® Hemoglobin A1c linearity set are determined. The set may contain standard samples to check linearity and verify calibration of commercial instruments for HbA1c assays (FIG. 6b). Target values of HbA1c for different platforms provided on the Bio-Rad technical data sheet along with the values determined by the MEA chip platform provided in the present disclosure are plotted. As shown in FIG. 6b, the values for National Glycohemoglobin Standardization Program (NGSP)-based methods are grouped higher than those for International Federation of Clinical Chemistry and Laboratory Medicine (IFCC)-based methods (typically +1.5-2.0%). NGSP-based methods measure the percentage of HbA1c in total HbA at the protein level, while IFCC-based methods measure the ratio between glycated and nonglycated hexapeptides of HbA at the peptide level after enzymatic digestions. The values from the LC-MS assay are consistent with these target values. Therefore, the LC-MS assay using a MEA chip as provided herein is suitable for quantifying protein glycation as glycemia markers for diabetes. It is further confirmed that the HbA1c values determined by the assay provided herein are consistent with those obtained using conventional methods. As shown in FIGS. 6c and 6d, results for the 8 samples from T2D subjects agree very well with those obtained by the commercial Tosoh G7 HPLC platform (NGSP method) (FIG. 6c: Pearson's correlation, r=0.9695, p<0.0001, two-tailed; and FIG. 6d: Bland-Altman Plot, limit of agreement (LoA), p<0.0500).

(3) Monitoring Glycemia

Figure 7A:
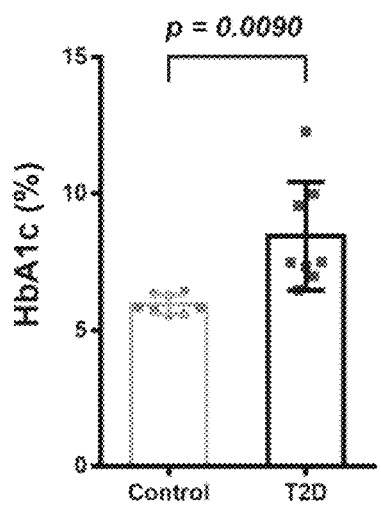
FIGS. 7a-7f show the application of an example top-down-proteomics-centric assay for monitoring glycemia in a subject using small volumes of blood samples.
Figure 7B:
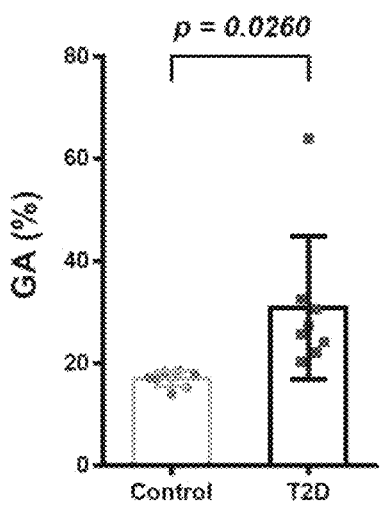
Figure 7C:
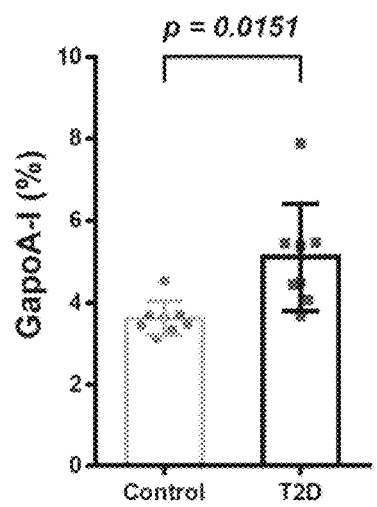
Figure 7D:
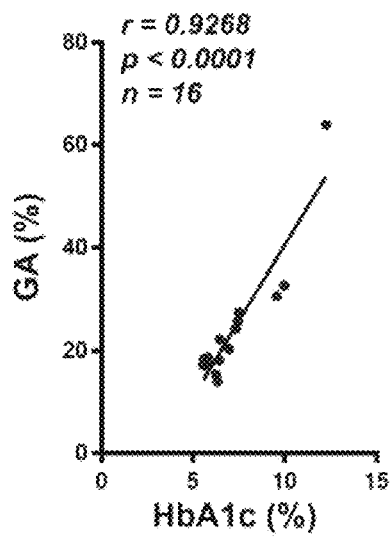
Figure 7E:
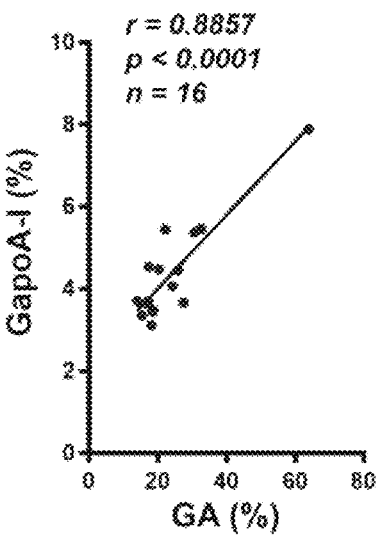
Figure 7F:
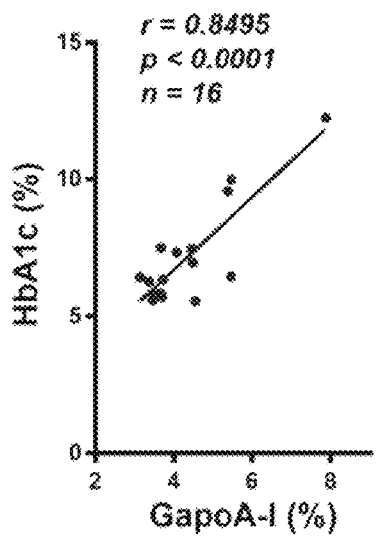

Fresh blood samples from a total of 16 subjects (8: healthy controls; 8: Type 2 diabetes, T2D) are analyzed. Values of HbA1c, GA, and GapoA-I between controls and T2D subjects are compared (FIGS. 7a-7c). The mean values are significantly higher in T2D subjects than in controls, with 8.44% and 5.95% for HbA1c, 30.93% and 17.05% for GA, and 5.10% and 3.63% for GapoA-I, respectively. Further, controls and T2D subjects can completely segregated by using these markers (Student's t-test, p=0.0090, 0.0260, 0.0151 for HbA1c, GA, and GapoA-I, respectively). Relationship between each two of these three markers is then evaluated for the total 16 samples analyzed (FIGS. 7d-7f). Strong correlation is seen for each pair of markers, with r=0.9268, 0.8857, and 0.8495 (Pearson's correlation, p<0.0001, two-tailed), for HbA1c and GA, GA and GapoA-I, and GapoA-I and HbA1c, respectively. Based on the average in vivo lifetime of their unmodified proteins, HbA1c, GA, GapoA-I can manifest the average blood glucose level over a period of 2-3 months, 2-3 weeks, and 1-2 days, respectively. Therefore, the degree of mutual correlations matches the degree of difference in timescales that these markers represent.

Figure 8A:
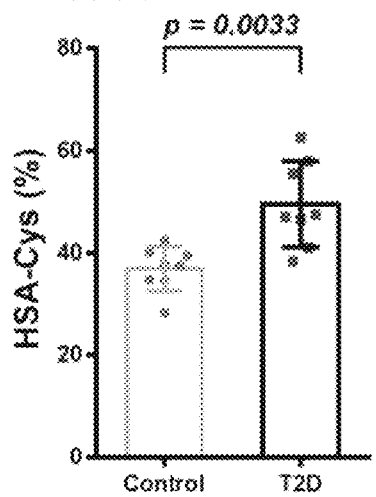
FIGS. 8a-8e show the application of an example top-down-proteomics-centric assay for concurrently monitoring oxidative stress and cardiovascular risks in a subject using small volumes of blood samples.
Figure 8B:
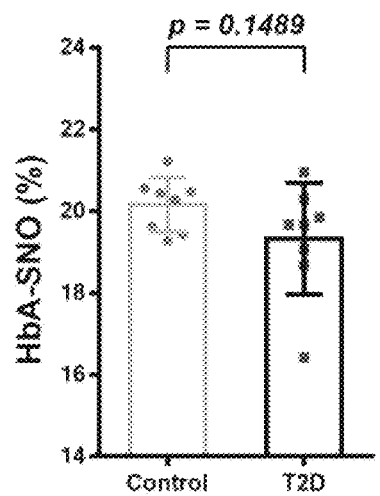
Figure 8C:
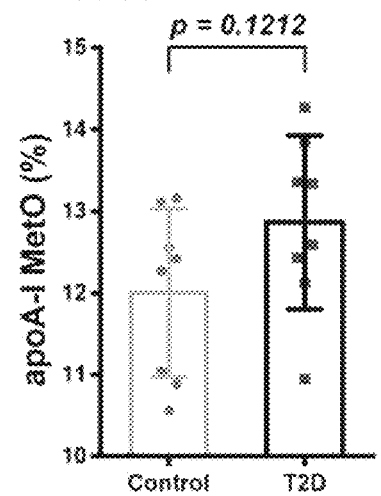
Figure 8D:
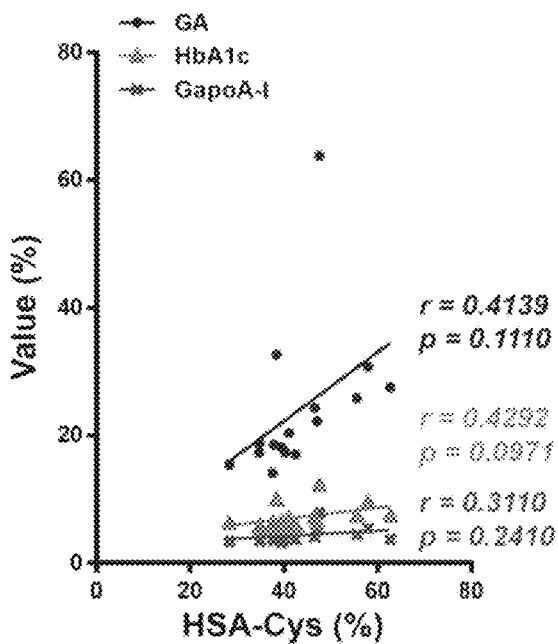
Figure 8E:
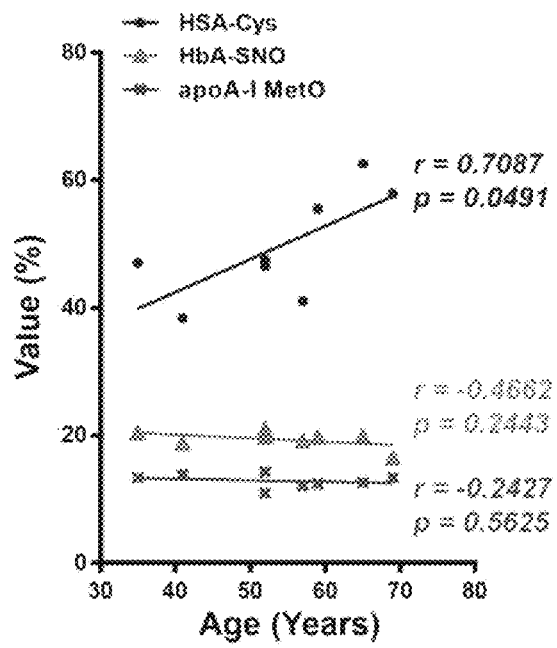
Figure 9:
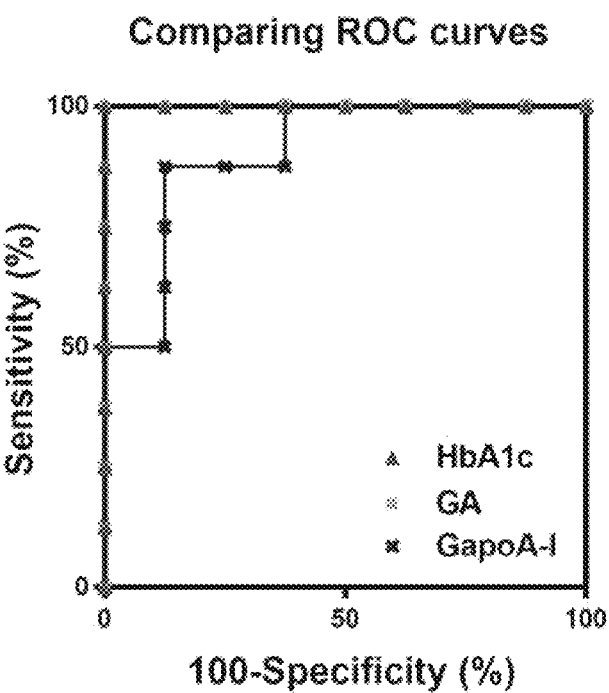
FIG. 9 shows the receiver operating characteristic (ROC) curve for normal control and T2D subjects. An area of 1 for both HbA1c and GA tests (p=0.0008) and an area of 0.9063 for GapoA-I test (p=0.0063) are obtained, which shows excellent performance (both sensitivity and specificity) of the example assay for all three markers HbA1c, GA, and GapoA-I for diabetes monitoring.

(4) Providing Additional Information about Oxidative Stress and Cardiovascular Risks There is a strong interplay between oxidative stress and diabetes, and the most severe consequences of diabetes are cardiovascular diseases including atherosclerosis. As already shown in FIG. 5, the LC-MS assay can concurrently detect HSA-Cys, HbA-SNO, and apoA-I MetO, which are example protein markers for oxidative stress in plasma, hypoxic vasodilation, and oxidative status of high-density lipoprotein cholesterol (HDL), respectively. Values of these markers for controls and T2D subjects are compared (FIGS. 8a-8c). A significant increase of HSA-Cys in T2D compared to controls (mean=49.59% vs. 36.96%, p=0.0033, Student's t-test), an insignificant decrease of HbA-SNO (mean=20.17% vs. 19.33%, p=0.1489, Student's t-test), and an insignificant increase of apoA-I MetO (mean=12.01% vs. 12.87%, p=0.1212, Student's t-test) are observed. These results suggest a higher oxidative stress (via HSA-Cys) and possible perturbation of vasodilation functions (via GapoA-I and HbA-SNO) in T2D subjects. The inter-correlation between the oxidative stress interrelated and hyperglycemia in diabetes is then evaluated. Some non-significant correlations between HSA-Cys and blood glycemia markers HbA1c, GA, and GapoA-I are observed, with the values for Pearson's correlation (two-tailed), r=0.4139, p=0.1110; r=0.4292, p=0.0971; and r=0.3110, p=0.2410; for GA, HbA1c, and GapoA-I, respectively (FIG. 8d). The possible cause of increased oxidative stress in T2D is then investigated. Values of HSA-Cys, HbA-SNO, and apoA-I MetO against the ages available for the 8 T2D subjects are plotted and shown in FIG. 8e. A significant correlation between the age and HSA-Cys (Pearson's correlation, r=0.7087, p=0.0491, two-tailed) is observed, suggesting an increased oxidative stress during aging, which is consistent with the free-radical theory of aging.

Figure 10:
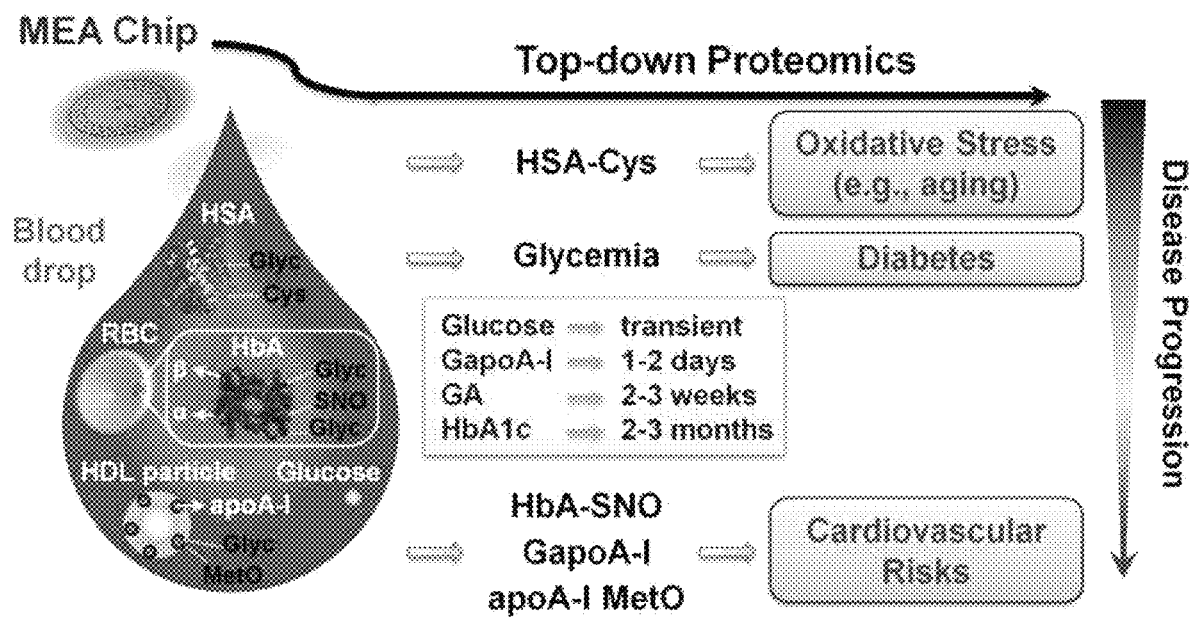
FIG. 10 shows an example scheme for rapid and multidimensional monitoring of diabetes using a drop of blood. The example top-down-proteomics-centric assay enabled by a MEA chip can concurrently monitor longitudinal markers for glycemia (glucose, GapoA-I, GA, and HbA1c), oxidative stress (HSA-Cys), and cardiovascular risks (HbA-SNO, GapoA-I, and apoA-I MetO) in a subject, thereby contributing to the elucidation of initiation, progression, and therapeutic responses of diabetes.

(5) Rapid and Multidimensional Monitoring of Diabetes Starting from a Drop of Blood (FIG. 10)

Assays of the present disclosure can analyze small molecules, proteins, and protein post-translational modifications with common pathophysiological themes (high blood glucose and oxidative stress) that may play important roles in diabetes, using a single LC-MS experiment without complex sample preparation. This can enable the rapid and multidimensional monitoring of diabetes as well as other diseases, in some cases from a biological sample of substantially small volume.

(6) Minimizing Blood Sample Preparation Prior to LC-MS Analysis

Dynamic range is a challenging issue for both bottom-up proteomics and top-down proteomics. Three most abundant blood proteins are utilized in an example assay described herein for diabetes monitoring. No complex sample preparation such as immunoaffinity enrichment is required herein, and therefore the assay is not constrained by the dynamic range issue that has long plagued other assays for analyzing low-abundance proteins. However, the assays provided herein may also contain an extraction segment that allows for enrichment of additional low-abundance species for diabetes monitoring if needed. For conventional microbore/nanobore LC-MS systems, electrospray emitters are not monolithically coupled with LC columns, but instead are connected via capillary tubing with proper fittings, which results in dead volumes and post-column losses. In addition, the micrometer-size nanospray emitters may be easily clogged by plasma proteins because they are denatured under high ESI voltage and high organic solvents when eluted from the C4 column. This contributes to the low robustness and lack of reproducibility for nanospray MS and renders it unsuitable for clinical applications. In contrast, the fabricated emitters provided herein are monolithically interfaced with the on-chip and online C4 column on the Si-based MEA chip, which significantly reduces the clogging, minimizes the dead-volume, thereby having an increasing sensitivity and robustness while maintaining the specificity and accuracy of the LC-MS assay. The MEA chip provided herein may sustain the same level of performance after over 100 consecutive LC-MS runs of crude whole blood samples with essentially no sample cleanup. As discussed elsewhere herein, implementation of multiplex and multi-function on-chip columns (e.g., 24-plex) on the MEA chip may further increase the throughput of the assay for parallel analysis.

Diabetes (including Type 1, Type 2, and Gestational) is a very complex and heterogeneous disease. The mechanisms underlying each subtypes of diabetes, and how the oxidative stress induces both microvascular and cardiovascular complications of diabetes, remain elusive. The oxidative stress can be directly monitored by using one plasma marker (e.g., HSA-Cys). Similarly, possibly cardiovascular risks of diabetes can be evaluated by using one or more markers such as, for example, HbA-SNO, GapoA-I, and apoA-I MetO, concurrently with the corresponding status of longitudinal blood glycemia (glucose, HbA1c, GA, and GapoA-I). One of the major consequences of diabetes is cardiovascular diseases (CVD). In fact, heart attacks account for majority of the deaths in subjects with diabetes. Both glycation and oxidation of apoA-I may possibly affect the functions of HDL (a key player in CVD). Therefore, the assay provided herein may facilitate longitudinal investigations of the initiation, progression, and consequences of diabetes for each subject, and thus provide new insights at the molecular (proteins), cellular (RBCs), and tissue (blood) levels. This in turn may help dissect the mechanisms underlying diabetes and provide better disease management. The new FDA Guidance to Industry for the development of new anti-diabetes therapies mandates that their cardiovascular risks be evaluated concurrently for drug safety, in addition to demonstrating their efficacy of lowering and maintaining blood glucose levels. Since the method provided herein may simultaneously measure multiple biomarkers for oxidative stress, blood glycemia, and cardiovascular risks of subjects, using a single LC-MS run starting from a single drop of blood, it may therefore be used in conjunction with cardiac markers such as hERG (human potassium ion channel) in clinical trials to facilitate new drug developments. It can further be utilized for routine monitoring of patients, for example, in response to different treatment regimens, for personalized management and treatment of diabetes.

The present disclosure provided a rapid, sensitive, and specific, top-down-proteomics-centric method and system for monitoring multiclass biomarkers of diabetes starting from a drop of blood (i.e., ≤5 µL). If combined with the micro-sampling of blood (e.g., using calibrated capillary tubes), and validated with a larger population of subjects in conjunction with prospective clinical studies to determine the limit of detection (LOD), inter- and intra-patient variations, and comparability with the existing commercial platforms, the method and system described herein may contribute to the long-term management of diabetes, and promote the clinical applications of top-down proteomics in theranostics of other diseases, for example, cancer and neurodegenerative diseases.

Example 7

Cancer Diagnosis

A blood sample comprising Zn-α2 glycoprotein (ZAG) is collected from a subject suspected of having a prostate cancer and serum is isolated from the blood sample. A volume of 4 µL of the processed blood sample is injected into a microfluidic device having a separation channel and a multi-nozzle emitter via a sample inlet. The injected sample is then directed to the sample separation channel which then separates or isolates different substances included in the sample. The isolated substances are then directed from the separation channel to the emitter which uses electrical energy to assist the ionization for each of the isolated substances before they are subjected to mass spectrometric (MS) analysis. Each of the ionized substances is then detected and analyzed by a MS detector. Quantity or concentration of Zn-α2 glycoprotein (ZAG) in the blood of the subject is then compared with those of controls. A higher-level of Zn-α2 glycoprotein (ZAG) indicates the presence of the cancer.

Example 8

Determining the Progression of Inflammatory Diseases

A blood sample comprising a plurality of endothelial adhesion molecules (e.g., intercellular adhesion molecule (ICAM), vascular cell adhesion molecule (VCAM), E-selectin etc.) is collected from a patient with an inflammatory disease. An aliquot of unprocessed blood sample is injected into a microfluidic device comprising a sample separation channel and a multi-nozzle emitter. The endothelial adhesion molecules contained in the blood sample are separated into a number of subsets and directed to a Mass Spectrometry (MS) detector. Each subset of the molecules are identified and analyzed by the detector. The presence of soluble forms of these adhesion molecules (sICAM, sVCAM, and sE-selectin) signals the progression of the disease.

Example 9

Early Diagnosis and Determining the Progression of Alzheimer's Disease

Alzheimer's disease (AD) is a devastating neurodegenerative disease that affects more than 35 million people worldwide, and this number is expected to reach more than 115 million by the year 2050. Recent disappointing clinical trials of bapineuzumab and solanezumab in AD treatment further aggravate the problem. The microfluidic chips disclosed herein may serve as a top-down proteomics platform for high-throughput and multiplex analysis of small volumes of human blood samples (e.g., plasma) and CSF for discovering new AD biomarkers.

Methods and systems provided herein are not limited to particular sequences, expression vectors, enzymes, host microorganisms, reagents or processes, as such may vary. It is also to be understood that the terminology used herein is for purposes of describing particular embodiments only, and is not intended to be limiting.

As used herein, the singular forms "a", "an", and "the" include plural references unless the context clearly dictates otherwise.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A microfluidic device, comprising:
   a fluid channel comprising an enrichment region and a separation region downstream of said enrichment region; and
   an emitter downstream of and in fluid communication with said fluid channel, said emitter disposed between a first layer and a second layer, and said fluid channel disposed between a third layer and said second layer,
   wherein said enrichment region is configured to (i) receive a solution comprising a plurality of biomarkers and (ii) concentrate said plurality of biomarkers to yield a concentrated solution comprising said plurality of biomarkers, and
   wherein said separation region is configured to (i) receive said concentrated solution comprising said plurality of biomarkers and (ii) separate said plurality of biomarkers.

2. The microfluidic device of claim 1, wherein said microfluidic device is monolithic.

3. The microfluidic device of claim 1, wherein said first layer or said second layer comprises a semiconductor.

4. The microfluidic device of claim 1, wherein said enrichment region has a different dimension than said separation region.

5. The microfluidic device of claim 1, wherein said emitter comprises a nozzle.

6. The microfluidic device of claim 5, further comprising a base tube in fluid communication with said fluid channel, wherein said nozzle extends from said base tube having a larger cross-sectional dimension than said nozzle.

7. The microfluidic device of claim 5, wherein said nozzle has a cross-sectional dimension that is less than or equal to about 50 micrometers.

8. The microfluidic device of claim 5, wherein said nozzle is a nanotube or a microtube.

9. The microfluidic device of claim 5, wherein said emitter comprises a plurality of nozzles, which plurality of nozzles comprises said nozzle.

10. The microfluidic device of claim 1, wherein said enrichment region or said separation region comprises a separation medium.

11. The microfluidic device of claim 10, wherein said separation medium comprises beads.

12. The microfluidic device of claim 11, wherein said beads have a cross-sectional dimension from about 1 micrometer to 50 micrometers.

13. The microfluidic device of claim 1, wherein said enrichment region is dimensioned to receive said solution having a volume that is less than or equal to about 50 microliters.

14. A system, comprising:
    a microfluidic device, comprising:
       a fluid channel comprising an enrichment region and a separation region downstream of said enrichment region; and
       an emitter downstream of and in fluid communication with said fluid channel, said emitter disposed between a first layer and a second layer, and said fluid channel disposed between a third layer and said second layer,
       wherein said enrichment region is configured to (i) receive a solution comprising a plurality of biomarkers and (ii) concentrate said plurality of biomarkers to yield a concentrated solution comprising said plurality of biomarkers, and
       wherein said separation region is configured to (i) receive said concentrated solution comprising said plurality of biomarkers and (ii) separate said plurality of biomarkers; and
    a detector operatively coupled to said emitter, which detector is configured to generate signals that are indicative of a presence of said plurality of biomarkers.

15. The system of claim 14, further comprising a computer processor coupled to said microfluidic device or said detector.

16. The system of claim 15, wherein said computer processor is programmed to (i) direct said solution through said fluid channel to said emitter under conditions sufficient to permit said plurality of biomarkers to be separated in said fluid channel, (ii) direct at least a portion of said plurality of biomarkers separated in (i) from said emitter to said detector, wherein said detector generates signals upon contact with said at least said portion of said plurality of biomarkers, and (iii) detect a presence of said at least said portion of said plurality of biomarkers based on said signals generated in (ii) to detect said presence of said plurality of biomarkers.

17. The system of claim 16, wherein said computer processor is programmed to identify a disease in a subject based on said presence of said plurality of biomarkers.

18. The system of claim 17, wherein said computer processor is programmed to detect said at least said portion of said plurality of biomarkers at multiple time points to monitor a progression of said disease in said subject.

19. The system of claim 15, wherein said third layer is configured to monitor an on-device process.

20. The system of claim 19, wherein said computer processor is programmed to monitor said on-device process in real-time.

21. The system of claim 17, wherein said disease is Alzheimer's disease.

* * * * *